United States Patent
Leipzig et al.

(10) Patent No.: US 10,335,490 B2
(45) Date of Patent: Jul. 2, 2019

(54) FLUORINATED POLYMERIZABLE HYDROGELS FOR WOUND DRESSINGS AND METHODS OF MAKING SAME

(71) Applicant: The University of Akron, Akron, OH (US)

(72) Inventors: Nic Leipzig, Hudson, OH (US); Asanka Wijekoon, Cuyahoga Falls, OH (US)

(73) Assignee: The University of Akron, Akron ( * ) Notice: Subject to any disclaimer, the term of this patent is extended or adjusted under 35 U.S.C. 154(b) by 945 days.

(21) Appl. No.: 14/374,563

(22) PCT Filed: Jan. 25, 2013

(86) PCT No.: PCT/US2013/023183
§ 371 (c)(1),
(2) Date: Jul. 25, 2014

(87) PCT Pub. No.: WO2013/112863
PCT Pub. Date: Aug. 1, 2013

(65) Prior Publication Data
US 2015/0018433 A1    Jan. 15, 2015

Related U.S. Application Data

(60) Provisional application No. 61/590,379, filed on Jan. 25, 2012.

(51) Int. Cl.
| | | |
|---|---|---|
| A61K 47/36 | (2006.01) | |
| A61L 15/28 | (2006.01) | |
| A61L 15/44 | (2006.01) | |
| A61L 15/60 | (2006.01) | |
| C08B 37/00 | (2006.01) | |
| C08B 37/08 | (2006.01) | |
| C08F 220/54 | (2006.01) | |
| C08L 33/24 | (2006.01) | |
| C08L 5/08 | (2006.01) | |

(52) U.S. Cl.
CPC ............ *A61K 47/36* (2013.01); *A61L 15/28* (2013.01); *A61L 15/44* (2013.01); *A61L 15/60* (2013.01); *C08B 37/00* (2013.01); *C08B 37/003* (2013.01); *C08F 220/54* (2013.01); *C08L 5/08* (2013.01); *C08L 33/24* (2013.01); *A61L 2300/412* (2013.01)

(58) Field of Classification Search
CPC combination set(s) only.
See application file for complete search history.

(56) References Cited

U.S. PATENT DOCUMENTS

| | | | |
|---|---|---|---|
| 4,618,649 A | 10/1986 | Ofstead | |
| 4,954,587 A | 9/1990 | Mueller | |
| 5,155,194 A * | 10/1992 | Kossmehl | C08F 220/22 264/1.1 |
| 5,214,452 A | 5/1993 | Kissmehl | |
| 5,739,121 A * | 4/1998 | Wiebe | A61K 47/48969 424/9.35 |
| 5,824,335 A * | 10/1998 | Dorigatti | D04H 1/46 424/443 |
| 2003/0199687 A1* | 10/2003 | Yalpani | C08B 11/06 536/56 |
| 2011/0134387 A1 | 6/2011 | Samuel et al. | |

FOREIGN PATENT DOCUMENTS

| | | | |
|---|---|---|---|
| CN | 101503491 | 8/2009 | |
| EP | 0050934 B1 | 5/1986 | |
| EP | 0188110 A1 | 7/1986 | |
| EP | 0253515 | 1/1988 | |
| EP | 0493320 | 7/1992 | |
| WO | WO-0016818 A1 * | 3/2000 | ........... A61K 31/728 |
| WO | 2011022680 | 2/2011 | |

OTHER PUBLICATIONS

Totani et al. Biochem. 2009, 48, 2933-2940.*
Berkel et al. ChemBioChem 2007, 8, 1504-1508.*
Wijekoon et al. Acta. Biomaterialia 2013, 9, 5653-5664 (Year: 2012).*
Fondriest Environmental, Inc. "Dissolved Oxygen." Fundamentals of Environmental Measurements. Nov. 19, 2013. Web. < http://www.fondriest.com/enviromental-measurements/parameters/water-quality/dissolved-oxygen/>. (Year: 2013).*
Fedorovich et al. "Scaffold Porosity and Oxygenation of Printed Hydrogel Constructs Affect Functionality of Embedded Osteogenic Progenitors." Tissue Eng. Part A 2011, 17, 2473-2486. (Year: 2011).*
GPonline "Oxygen-concentrating wound dressing delivers a breath of fresh air to hard-to-heal wounds." Mar. 28, 2007. Web. < https://www.gponline.com/oxygen-concentrating-wound-dressing-delivers-breath-fresh-air-hard-to-heal-wounds/article/932183>. (Year: 2007).*
Atsushi Matsuda, et al., Fluorinated Water-Swollen Hydrogels with Molecular and Supramolecular Organization, Macomoleculs, vol. 22, No. 7, 2531-2538 (Apr. 2010).
Sang-Yeon Shim, et al., Photocurable Florinated Methacrylates: Synthesis and Polymerization, Macromolecular symposia, vol. 277, No. 1, 201-206 (Mar. 2009).

* cited by examiner

*Primary Examiner* — Amanda L Aguirre
(74) *Attorney, Agent, or Firm* — Renner Kenner Greive Bobak Taylor & Weber

(57) ABSTRACT

Fluorinated hydrogels are used to dissolve oxygen or other oxygenated small molecules. The fluorinated hydrogels may release the dissolved oxygen or other oxygenated small molecules upon exposure to an environment of lower tension. The fluorinated hydrogels have a particular application in wound healing, where the fluorinated hydrogels may be used as a wound dressing.

20 Claims, 17 Drawing Sheets a. Ali5F b. Ar5F c. Ali15F

FLUORINATED POLYMERIZABLE HYDROGELS FOR WOUND DRESSINGS AND METHODS OF MAKING SAME

CROSS-REFERENCE TO RELATED APPLICATION

This application claims priority to U.S. Provisional Patent Application No. 61/590,379 filed on Jan. 25, 2012, the contents of which are incorporated herein by reference.

FIELD OF THE INVENTION

One or more embodiments of this invention are directed to fluorinated hydrogels, methods of preparing fluorinated hydrogels, methods of loading oxygen and oxygenated small molecules within fluorinated hydrogels, methods of releasing oxygen and oxygenated small molecules from loaded fluorinated hydrogels, and uses for fluorinated hydrogels.

BACKGROUND OF THE INVENTION

An oxygen rich environment is vital for wound healing as well as for regenerative medicine. Numerous experimental and clinical findings have established that oxygen therapy (hyperbaric, topical or dressing) can provide significant benefits to promote and accelerate tissue regeneration and healing in both acute and chronic wounds. The preferred treatment of large slow healing wounds consists of debridement, which produces widely varied results. Oxygen treatment has been demonstrated to promote healing by enhancing metabolism, extracellular matrix (ECM) synthesis and oxygenation across the wound from a supportive matrix has yet to be developed. Thus, there is significant need for enabling platform technologies in the area of wound care to support regenerative levels of oxygenation in a single total package.

SUMMARY OF THE INVENTION

A first embodiment of this invention provides a hydrogel comprising a crosslinked polymer, wherein the polymer has a pendant fluorine group.

A second embodiment provides a hydrogel as in the first embodiment, wherein the polymer has a pendant acetylamino group.

A third embodiment provides a hydrogel as in either the first embodiment or the second embodiment, wherein the polymer has a pendant amino group.

A fourth embodiment provides a hydrogel as in any of the first through third embodiments, wherein the crosslinked polymer is selected from the group consisting of polyethylene glycol, poly(N-isoproylacrylamide), polyacrylamide, peptides, and combinations thereof.

A fifth embodiment provides a hydrogel as in any of the first through fourth embodiments, wherein the crosslinked polymer is a polysaccharide such that the pendant fluorine group is attached to a polysaccharide chain.

A sixth embodiment provides a hydrogel as in any of the first through fifth embodiments, wherein the polysaccharide is selected from the group consisting of chitosan, dextran, hyaluric acid, agarose, and combinations thereof.

A seventh embodiment provides a hydrogel as in any of the first through sixth embodiments, wherein the pendant fluorine group is selected from the group consisting of fluorocarbon groups; carbonyl groups defined by the formula:

where R is a fluorocarbon group; and carboxylate groups defined by the formula:

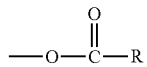

where R is a fluorocarbon group.

An eighth embodiment provides a hydrogel as in any of the first through seventh embodiments, wherein the pendant fluorine group is a fluorocarbon group defined by the formula:

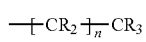

where each R is individually a hydrogen atom, or a fluorine atom.

A ninth embodiment provides a hydrogel as in any of the first through eighth embodiments, wherein the pendant fluorine group is a fluorocarbon group defined by the formula:

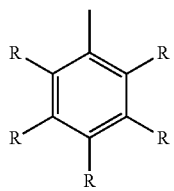

where each R is individually hydrogen atom, a fluorine atom, a hydroxyl group, a hydrocarbon group, or a fluorocarbon group.

A tenth embodiment provides a hydrogel in any of the first through ninth embodiments, wherein the pendant fluorine group is aromatic fluorocarbon group selected from the group consisting of:

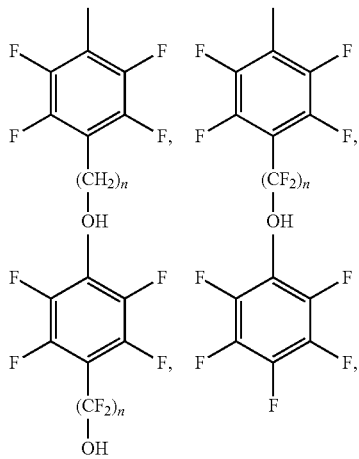

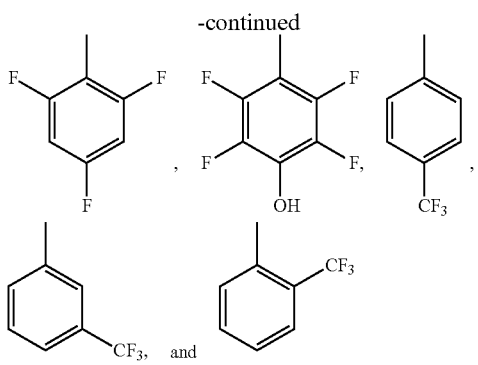

where n is 0 to 9.

An eleventh embodiment provides a hydrogel as in any of the first through tenth embodiments, wherein the pendant fluorine group is a carboxylate group selected from the group consisting of:

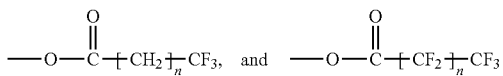

where n is 0 to 20.

A twelfth embodiment provides a hydrogel as in any of the first through eleventh embodiments, wherein the pendant fluorine group is attached to a polysaccharide chain via a polysaccharide unit defined by the formula:

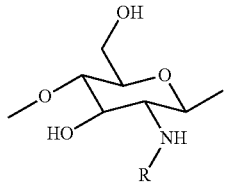

where R is a fluorine group.

A thirteenth embodiment provides a method of preparing a hydrogel comprising: crosslinking a polymer comprising a pendant fluorine group; and a crosslinkable group.

A fourteenth embodiment provides a method as in the thirteenth embodiment wherein the step of crosslinking the polymer is initiated by photo initiation.

A fifteenth embodiment provides a method as in either the thirteenth embodiment or fourteenth embodiment wherein the pendant fluorine group is selected from the group consisting of fluorocarbon groups; carbonyl groups defined by the formula:

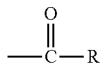

where R is a fluorocarbon group; and carboxylate groups defined by the formula:

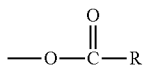

where R is a fluorocarbon group.

A sixteenth embodiment provides a method as in any of the thirteenth through fifteenth embodiments, wherein the pendant fluorine group is a fluorocarbon group defined by the formula:

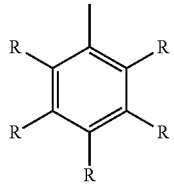

where each R is individually hydrogen atom, a fluorine atom, a hydroxyl group, a hydrocarbon group, or a fluorocarbon group.

A seventeenth embodiment provides a method as in any of the thirteenth through sixteenth embodiments, wherein pendant fluorine group is aromatic fluorocarbon group selected from the group consisting of:

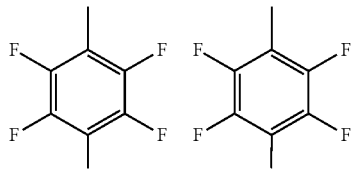

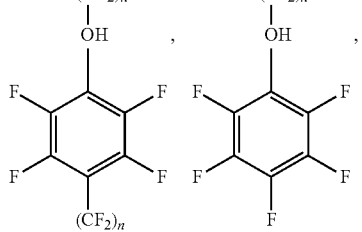

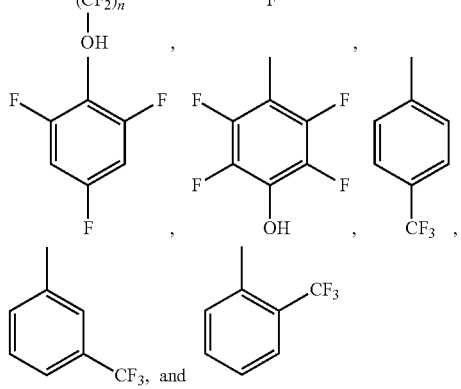

where n is 0 to 9.

An eighteenth embodiment provides a method as in any of the thirteenth through seventeenth embodiments, wherein the pendant fluorine group is a carboxylate group selected from the group consisting of:

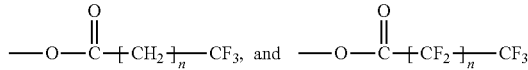

where n is 0 to 20.

A nineteenth embodiment provides a method as in any of the thirteenth through eighteenth embodiments, wherein polymer is selected from the group consisting of polyethylene glycol, poly(N-isoproylacrylamide), polyacrylamide, peptides, and combinations thereof.

A twentieth embodiment provides a method as in any of the thirteenth through nineteenth embodiments, wherein the polymer is a polysaccharide such that the pendant fluorine group is attached to a polysaccharide chain, and the cross-linkable group is attached to a polysaccharide chain.

A twenty-first embodiment provides a method as in any of the thirteenth through twentieth embodiments, wherein the polysaccharide polymer is a random copolymer of saccharide units defined by the formula:

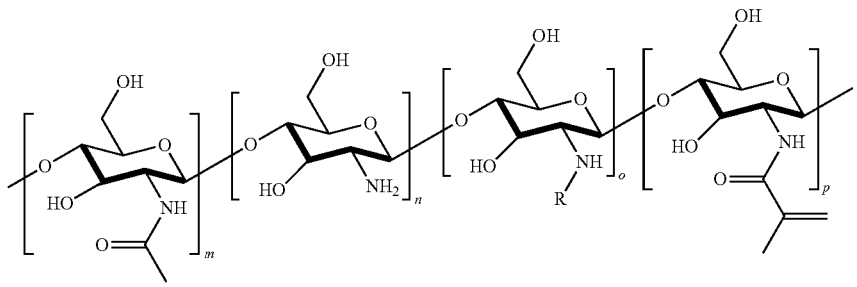

where R a fluorine group, m is about 10% to about 20% of the total saccharide units, n is about 15% to about 70% of the total saccharide units, o is about 10% to about 40% of the total saccharide units, and p is about 10% to about 25% of the total saccharide units.

DETAILED DESCRIPTION OF ILLUSTRATIVE EMBODIMENTS

Figure 1:
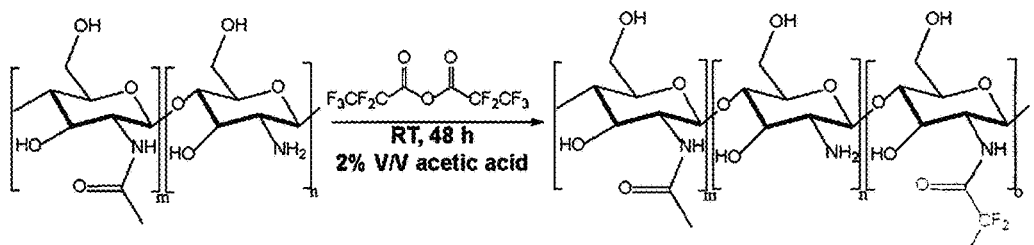
FIG. 1 provides a synthetic methodology for the creation of one or more embodiments.
Figure 1:
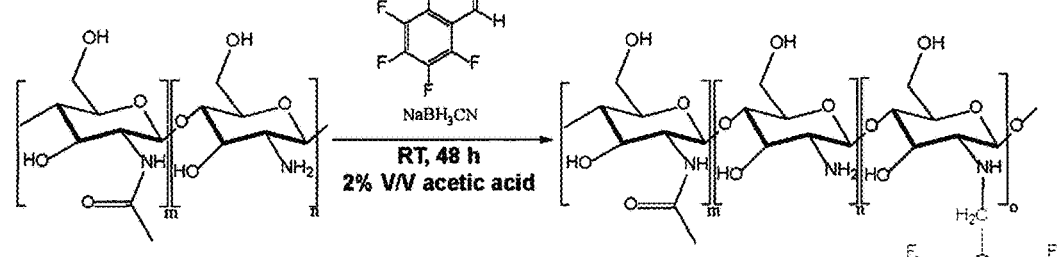
Figure 1:
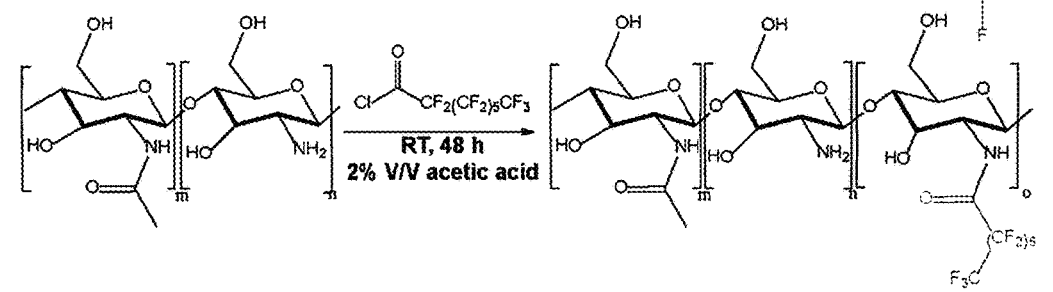

In one or more embodiments, the present invention provides a hydrogel formed of a crosslinked polymer containing a pendant fluorine group. The fluorines allow the hydrogel to dissolve oxygen, which can later be released from the hydrogel to an area of low oxygen concentration. In one or more embodiments, the hydrogel may release oxygen to a wound. In one or more embodiments the hydrogel includes acetylamino groups. In these or other embodiments, the hydrogel includes amino groups. For the purposes of this specification, the hydrogel formed of a crosslinked polymer having pendant fluorinated groups is referred to as a fluorinated hydrogel.

In one or more embodiments, the crosslinked polymer containing a pendant fluorine group is a fluorinated hydrogel that substantially comprises water. In one or more embodiments, the crosslinked polymer containing a pendant fluorine group is a fluorinated hydrogel that may comprise at least 90% water. In one or more embodiments, the crosslinked polymer containing a pendant fluorine group is a fluorinated hydrogel that may comprise at least 97% water. In one or more embodiments, the crosslinked polymer containing a pendant fluorine group is a fluorinated hydrogel that may comprise at least 99% water. For the purposes of this specification, the crosslinked polymer containing a pendant fluorine group may be referred to as a fluorinated hydrogel polymer.

With the understanding that that hydrogels are polymer matrices, or crosslinked polymers, that absorb water, in one or more embodiments, the fluorinated hydrogel is at least partially dried crosslinked polymer capable of absorbing aqueous-based mediums much like a sponge. Those of skill in the art may refer to this as swelling behavior. A fluorinated hydrogel that is at least partially dried may be referred to as a dried fluorinated hydrogel or a sponge. In one or embodiments, the dried fluorinated hydrogel may be substantially dehydrated or entirely dehydrated.

The fluorinated hydrogel may absorb oxygen when moved from an initial environment to an environment of higher oxygen tension. The fluorinated hydrogel upon exposure to an environment of lower oxygen tension may then release oxygen.

In its broadest sense, a fluorine group is to be understood as a group that includes at least one fluorine atom. In one or more embodiments the fluorine is bonded directly to a carbon atom. In one or more embodiments, the fluorine group is a pendant fluorine group. A pendant fluorine group is pendantly attached to a polymer or a hydrogel. In other words, a pendant fluorine group is a side chain that is attached to the main chain or backbone of a polymer or a hydrogel.

In one or more embodiments, the fluorine group may be a fluorocarbon group. In one or more embodiments, a fluorocarbon group may be a hydrocarbon group where one or more hydrogen atoms are substituted with a fluorine atom. Suitable fluorocarbon groups that can be substituted with fluorine atoms include alkyl groups such as methyl, ethyl, propyl, isopropyl, tert-butyl, n-butyl, sec-butyl, isopentyl, tertpentyl, n-pentyl, sec-pentyl, terthexyl, n-hexyl, isohexyl, and sec-hexyl. For the purpose of this disclosure, the term fluorocarbon and perfluorocarbon can be used interchangeably. For simplicity, perfluorocarbon may be abbreviated PFC.

In one or more embodiments a fluorocarbon group may be defined by the formula:

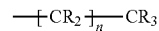

where each R is individually a hydrogen atom, or a fluorine atom. In one or more embodiments, n may range from 0 to 20. In one or more embodiments, n may range from 1 to 9. In one or more embodiments, n may range from 6 to 8.

Specific examples of fluorocarbon groups include —$CF_3$, —$(CF_2)_n$—$CF_3$, —$(CF_2)_n$—$CF_3$, —$(CH_2)_n$—$CF_3$, and —$(CH_2)_n$—$(CF_2)_n$—$CF_3$. In one or more embodiments, n may range from 0 to 20. In one or more embodiments, n may range from 1 to 9. In one or more embodiments, n may range from 6 to 8.

In one or more embodiments, the fluorocarbon may be an aromatic fluorocarbon group. In one or more embodiments, an aromatic fluorocarbon group may be defined as an aromatic group where one or more hydrogen atoms are substituted with a fluorine atom. In one or more embodiments an aromatic fluorocarbon group may be defined by the formula:

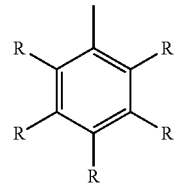

where each R is individually hydrogen atom, a fluorine atom, a hydroxyl group, a hydrocarbon group, or a fluorocarbon group. Specific examples of aromatic fluorocarbon groups include

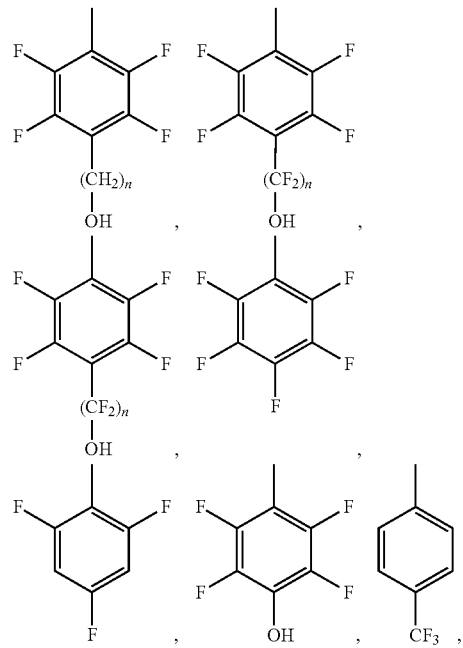

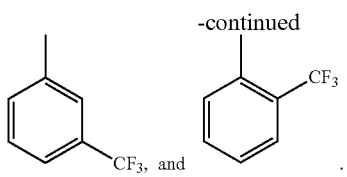

In one or more embodiments, n may range from 0 to 9. In one or more embodiments, n may range from 1 to 6. In one or more embodiments, n may range from 2 to 4.

In one or more embodiments, the fluorine group may be a carbonyl group defined by the formula:

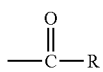

where R is a fluorocarbon group. Specific examples of carbonyl defined by the above formula include groups include

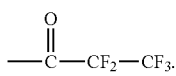

In one or more embodiments, the fluorine group may be a carboxylate group defined by the formula:

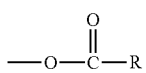

where R is a fluorocarbon group. Specific examples of carboxylate groups defined by the above formula include

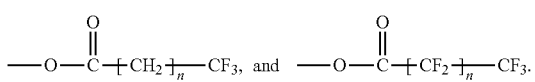

In one or more embodiments, n may range from 0 to 20. In one or more embodiments, n may range from 1 to 9. In one or more embodiments, n may range from 6 to 8.

In one or more embodiments, the fluorine group may be first attached to a monomer that may be polymerized optionally with other co-monomers. In other embodiments, the fluorocarbon group may be attached to a preformed polymer or hydrogel.

In one or more embodiments, the fluorine group may be attached to a monomer, polymer or hydrogel that includes a reactable moiety. Suitable reactable moieties include hydroxyl groups, amino groups, carboxylic acid groups, sulfhydryl groups, maleimide groups, and tyrosine groups. In these or other embodiments a fluorine compound is attached to the monomer, polymer or hydrogel through the reactable moiety. A suitable fluorine compound may be selected from compounds that include a fluorine group and a group selected from halogen groups, carboxylic acid groups, alcohol groups, aldehyde groups, and acyl halides. Other suitable fluorine compounds are acid anhydrides of fluorinated carboxylic acids.

In one or more embodiments, a fluorinated hydrogel may be formed by crosslinking a polymer that includes a fluorine group and a group capable of being crosslinked. In one or more embodiments, the group capable of being crosslinked may be first attached to a monomer that may be polymerized optionally with other co-monomers. In these or other embodiments, the fluorinated group may be attached to a monomer and co-polymerized with the group capable of being crosslinked or added after the polymerization. In other embodiments, the group capable of being crosslinked may be attached to a preformed polymer. In these or other embodiments, the polymer may already contain fluorinated groups. In one or more embodiments, the fluorinated hydrogel may be attached before or after the formation of a hydrogel.

In one or more embodiments, a fluorinated hydrogel may be prepared by crosslinking the polymer with a radical initiator. Suitable radical initiators include azo compounds and organic peroxides. Examples of radical initiators may include ammonium persulfate, and sodium metabisulfite, or fixatives like gluraldehyde, formaldehyde, acetone, methanol, and ethanol In certain embodiments, the radical initiator employed to crosslink the polymer may be a photoinitiator. In these or other embodiments, a fluorinated hydrogel may be prepared by initiating a crosslinking reaction by exposing the crosslinker to light. Suitable photoinitiators include commonly used photoinitiators for biological applications. Examples of photoinitiators include 4-(2-hydroxyethoxy)phenyl-(2-hydroxy-2-propyl)ketone, 1-hydroxycyclohexyl benzophenone, and 2,2-dimethoxy-1,2-di(phenyl)ethanone.

In one or more embodiments, the group capable of being crosslinked is an alkene group. In one or more embodiments, an alkene group is a hydrocarbyl or substituted hydrocarbyl group that includes at least one carbon-carbon double bond. Substituted hydrocarbyl groups include groups where a carbon or a hydrogen is replaced with a heteroatom. Exemplary heteroatoms include nitrogen, oxygen, sulfur, phosphorus, chlorine, bromine, and iodine. In one or more embodiments, the alkene group is a vinyl group. In one or more embodiments, the alkene group is a $\alpha,\beta$-unsaturated carbonyl. Specific examples of alkene groups include methacrylic or acrylate groups.

In certain embodiments, a hydrogel may be prepared by crosslinking the polymer through Michael addition. In these or other embodiment, a crosslinking molecule with at least two nucleophilic groups can crosslink a polymer that contains alkene groups. A crosslinking molecule may be a molecule with at least two sulfhydryl groups.

In one or more embodiments, the group capable of being crosslinked is a sulfhydryl group. Those skilled in the art will recognize that a sulfhydryl group may also be referred to as a thiol group. Crosslinking is achievable via disulfide bonds which are formed from the oxidation of sulfhydryl (—SH) groups. In one or more embodiments, a separate crosslinking molecule can be added with sulfhydryls terminating either end to crosslink polymer chains together via the formation of two disulfide bonds. Examples of separate crosslinking molecules include, but are not limited to, short amino acid sequence/peptide, PEG, hydrocarbon chains. Aqueous conditions with a pH between 3 and 8 are preferred for stable covalent bond formation.

In one or more embodiments, the sulfhydryl group can react with a alkene group on another polymer chain or separate crosslinker molecule to form a covalent bond crosslink. Those skilled in the art will recognize this as Michael addition or Michael reaction. Aqueous conditions with a pH between 3 and 8 are preferred for stable covalent bond formation.

In one or more embodiments, the sulfhydryl group can react with a maleimide group on another polymer chain or separate cross linker molecule to form a covalent bond crosslink. Aqueous conditions with a pH between 3 and 8 are preferred for stable covalent bond formation.

In one or more embodiments, the group capable of being crosslinked is a tyrosine group. The tyrosine group can react with a tyrosine group on another polymer chain or separate crosslinker molecule to form a covalent bond crosslink. Suitable conditions for crosslinking are in the presence of horseradish peroxidase and peroxide ($H_2O_2$) at 1-50 mM.

In one or more embodiments, the fluorinated hydrogels are prepared by crosslinking a polymer comprising a crosslinkable group and a fluorine group. In one or more embodiments, the polymer further comprises an acetylamino group. In one or more embodiment, the acetylamino group may be pendently attached to the polymer. In these or other embodiments, the polymer further comprises an amino group. In one or more embodiment, the amino group may be pendently attached to the polymer. In one or more embodiments, the polymer is water soluble.

In one or more embodiments, the ratio of crosslinkable groups to fluorine groups is about 1:1 to 1:5 or 5:1. In one or more embodiments, the ratio of crosslinkable groups to fluorine groups is about 1:1 to 1:3 or 3:1. In one or more embodiments, the ratio of crosslinkable groups to fluorine groups is about 1:1 to 1:2 or 2:1.

The amount of fluorine groups may also be thought of in terms percent of substituted groups. In one or more embodiments, the polymer comprising a crosslinkable group and a fluorine group may contain 10% to 25% crosslinkable groups and 10% to 40% fluorine groups. In one or more embodiments, where the polymer comprising a crosslinkable group and a fluorine group further comprises an acetylamino group, the acetylamino group may be present up to 20%. In one or more embodiments, where the polymer comprising a crosslinkable group and a fluorine group further comprises an amino group, the amino group may be present from 15% to 70%.

In one or more embodiments, the polymers have a more have an average molecular weight of about 5,000 to 40,000 Da. In one or more embodiments, the polymers have a more have an average molecular weight of about 10,000 to 30,000 Da. In one or more embodiments, the polymers have a more have an average molecular weight of about 15,000 to 25,000 Da.

In one or more embodiments, polymers include those with a reactable moiety. Suitable reactable moieties include hydroxyl groups, amino groups, carboxylic acid groups, sulfhydryl groups, maleimide groups, tyrosine groups, or combinations thereof.

Exemplary polymers include polyethylene glycol, poly (N-isoproylacrylamide), polyacrylamide, peptides or a combination thereof.

In one or more embodiments, the polymer may be a polysaccharide. Exemplary polysaccharides include chitosan, dextran, hyaluronic acid, agarose, alginate, starch, cellulose, glycogen, carrageenans, galactomannans and combinations thereof.

In one or more embodiments, the polysaccharide is comprised of polymerized saccharide units. For the purpose of this specification a saccharide unit is a mer unit of a polysaccharide polymer. In one or more embodiments, the polysaccharide polymer can be comprised of saccharide units that have a functionality. In these or other embodiments, the polysaccharide polymer can comprise a saccharide unit that includes a fluorocarbon group and a saccharide unit that includes an alkene group. In one or more embodiments, the polysaccharide polymer may further comprise a saccharide unit that includes an acetylamino group. In these or other embodiments, the polysaccharide polymer may further comprise a saccharide unit that includes amino group.

In one or more embodiments, the polysaccharides may include a saccharide unit that includes a fluorocarbon group defined by the formula:

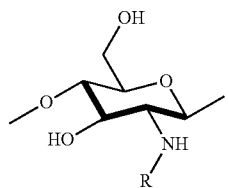

where R is a fluorine group.

In one or more embodiments, the polysaccharides may include a saccharide unit that includes a alkene group defined by one of the formula:

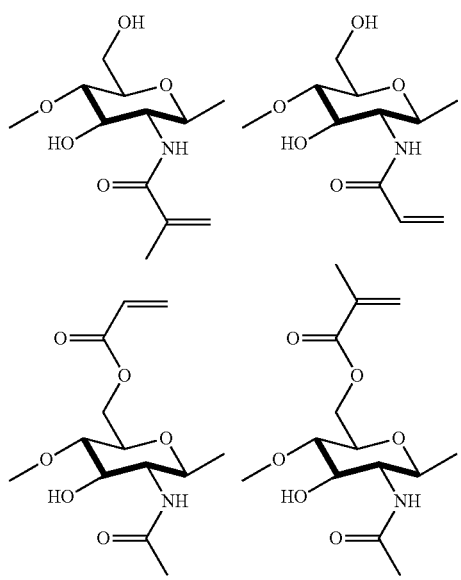

In one or more embodiments, the polysaccharides may include a saccharide unit that includes an acetylamino defined by the formula:

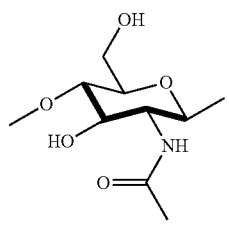

In one or more embodiments, the polysaccharides may include a saccharide unit that includes amino defined by the formula:

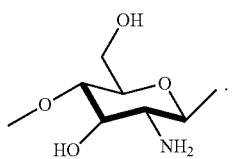

In one or more embodiments, the polysaccharide polymer is a random copolymer of saccharide units defined by the formula:

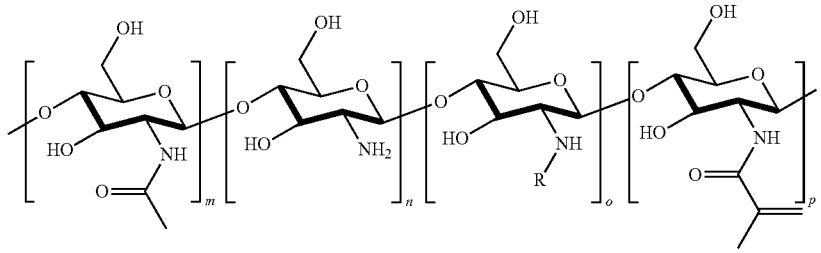

where R is a fluorine group, m is about 0% to about 20% of the total saccharide units, n is about 15% to about 70% of the total saccharide units, o is about 10% to about 40% of the total saccharide units, and p is about 10% to about 25% of the total saccharide units.

In one or more embodiments, the fluorinated hydrogel may be loaded with oxygen by placing a fluorinated hydrogel or a dehydrated polymer sponge comprising a crosslinked polymers containing a pendant fluorine group in an aqueous solution. Prior to or during the addition of the fluorinated hydrogel or a dehydrated polymer sponge comprising a crosslinked polymer containing a pendant fluorine group, oxygen may be added to the aqueous solution by bubbling oxygen gas through the solution or adding a oxygenated solution that contacts the polymer. The fluorinated hydrogel may also be loaded with oxygen by increasing the partial pressure of oxygen gas in the environment surrounding the fluorinated hydrogel.

In one or more embodiments, the fluorinated hydrogel has an oxygen uptake capacity. The oxygen uptake capacity refers to the partial pressure of oxygen absorbed by the fluorinated hydrogel per unit mass of the dried fluorinated hydrogel. In one or more embodiments, the fluorinated hydrogel may have an oxygen uptake capacity of at least 2 mmHg oxygen partial pressure ($P_{O_2}$)/mg polymer at 20° C. and 760 mmHgIn one or more embodiments, the fluorinated hydrogel may have an oxygen uptake capacity of at least 20 mmHg $P_{O_2}$/mg polymer at 20° C. and 760 mmHg. In one or more embodiments, the fluorinated hydrogel may have an oxygen uptake capacity of at least 20 mmHg $P_{O_2}$/mg polymer at 20° C. and 760 mmHg.

The use of fluorinated hydrogels is advantageous because the fluorinated hydrogel may be repeatedly loaded with dissolved oxygen and then release said oxygen. The fluorinated hydrogel's ability to be loaded with dissolved oxygen may be referred to as a regeneration cycle. In one or more embodiments, the fluorinated hydrogel may undergo 3 or more regeneration cycles with an oxygen capacity loss of less than 10%. In one or more embodiments, the fluorinated hydrogel may undergo 3 or more regeneration cycles with an oxygen capacity loss of less than 7%. In one or more embodiments, the fluorinated hydrogel may undergo 3 or more regeneration cycles with an oxygen capacity loss of less than 5%.

In one or more embodiments, the oxygen solubility of the fluorinated hydrogel may be improved by at least one order of magnitude over the oxygen solubility of the non-fluorinated hydrogel. Oxygen solubility may be measured using a dissolved oxygen sensor or other established colorimetric methods.

Fluorinated hydrogels dissolve $O_2$ as well as other oxygenated species, such as $CO_2$, CO and NO, by diffusion.

Thus fluorinated hydrogels can be utilized to not only deliver oxygen but to scavenge waste carbon dioxide gas or mitigate reactive oxygen species. The fluorinated groups of the fluorinated hydrogel may also be used to dissolve other molecules such as $CO_2$, CO, or NO alone or in combination with $O_2$. For example, a wound dressing may be prepared that will administer NO and $O_2$ simultaneously to a wound.

In one or more embodiments, the fluorinated hydrogel has advantageous hemostatic properties. In these or other embodiments, the fluorinated hydrogel may include amine groups. It is believed that the net positive charge do to free primary amines on chitosan leads to more protein adsorption which drives platelet recruitment and the whole healing pathway.

In one or more embodiment, a fluorinated hydrogel or sponge may be used to prepare a wound dressing. The fluorinated hydrogel or sponge may be cut to shape to prepare a wound dressing. Alternatively, a polymer containing a crosslinkable group and a pendant fluorine group may be placed in a mold and then crosslinked.

In one or more embodiments, a wound dressing prepared from a fluorinated hydrogel may be loaded with oxygen and then sealed in an airtight package. The wound dressing may then be stored without oxygen loss, and placed on a wound site at a later time.

In one or more embodiments, a wound dressing may be prepared by administering a polymer containing a pendant fluorine group to a wound site and then crosslinking the polymer to prepare a fluorinated hydrogel at the wound site. The fluorinated hydrogel may be loaded with oxygen before or after the crosslinking step.

In one or more embodiments, a wound dressing may be prepared from a sponge comprising a crosslinked polymer containing a pendant fluorine group. In one or more embodiments, the wound dressing prepared from a sponge may be hydrated and then applied to a wound. In other embodiments, the wound dressing prepared from a sponge may be hydrated by moisture secreted from the wound.

Wound dressings may optionally have a backing. In one or more embodiments, the wound dressing backing may provide one or more advantageous features such as rigidity impermeable gas exchange, and limited gas exchange with the open atmosphere. In these or other embodiments, an adhesive may be applied to the backing of the wound dressing.

In one or more embodiments, a oxygen loading of a fluorinated hydrogel may take place by chemical means. In these or other embodiments, a metal peroxide may be used in combination with the hydrogel to produce oxygen upon hydration. Examples of metal peroxides suitable for producing oxygen upon hydration include $CaO_2$, $MgO_2$ and combinations thereof.

In particular embodiments, a metal peroxide may be placed into a sealed membrane and upon hydration the metal peroxide will react to form and release oxygen. The sealed membrane may be attached to the fluorinated hydrogel. For example, a wound dressing may be prepared that includes a sealed membrane attached to a dried hydrogel. The wound dressing may optionally include a backing. Upon hydration of the membrane and dried fluorinated hydrogel oxygen is formed and released. The oxygen may then be dissolved by the fluorinated hydrogel. The sealed membrane may also be included separately and applied later to the hydrogel.

In one or more embodiments, the metal peroxide may be included in the fluorinated hydrogel. For example, the metal peroxide may be encapsulated along with in hydrogel at the time of crosslinking.

In light of the foregoing, it should be appreciated that the present invention significantly advances the art by providing a fluorinated hydrogel that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

1. Materials and Methods

Figure 2:
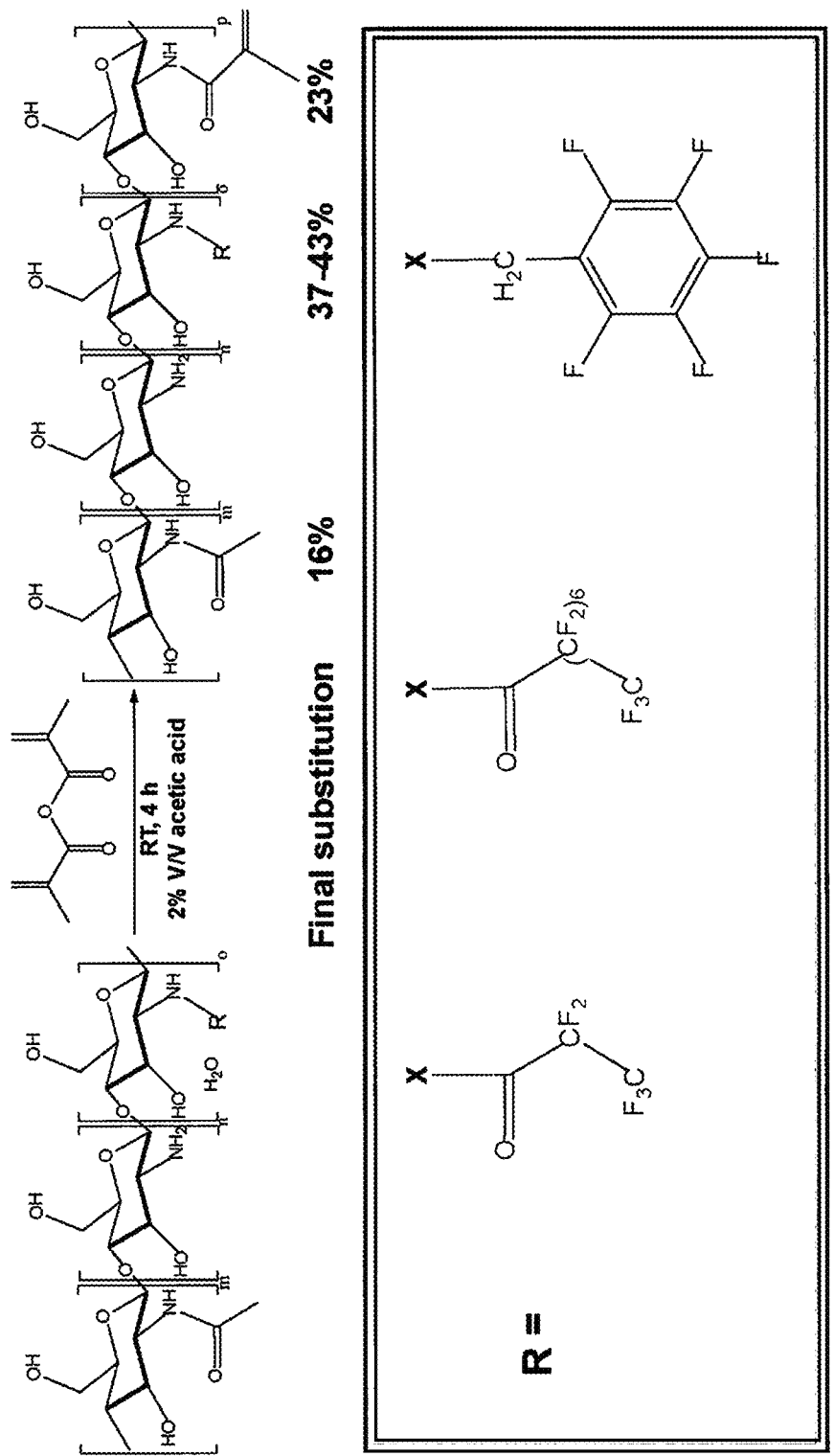
FIG. 2 provides a synthetic methodology for the creation of one or more embodiments.

Photopolymerizable methacrylamide chitosan (MAC) was synthesized by modifying medium molecular weight chitosan (MW 190,000-230,000 Da, Sigma-Aldrich, St. Louis, Mo.) with methacrylic anhydride (Sigma) to yield MAC containing 23% methacrylic groups. The degree of deacetylation of chitosan was determined by $^1$H NMR as described previously and found to be 84%. Briefly, MAC was dissolved in 0.25% DCl in $D_2O$ at 0.5% (w/v), then the 1H NMR spectrum recorded (Varian 400 MHz NMR spectrometer, Palo Alto, Calif.). The degree of methacrylation was calculated by comparing the integrated area of the H2-H6 peaks at 2.8-4.0 p.p.m. with that of the methylene peaks at 5.6 and 6.0 p.p.m. To add PFC moieties chitosan was first modified with fluorinated ligands (pentafluoropropionic anhydride, 2,3,4,5,6-pentafluorobenzaldehyde and pentadecafluorooctanoyl chloride) (Sigma-Aldrich) followed by methacrylic anhydride to yield fluorinated methacrylamidechitosans (MACFs). The synthetic methodology (FIG. 1 and FIG. 2) was formulated to enable creation of MACF hydrogels by radical polymerization.

1.1. Preparation of Pentafluoropropionic Anhydride Modified Methacrylamide Chitosan (MAC(Ali5)F)

Chitosan was first dissolved at 3% w/vin 2 vol. % acetic acid/water. A previously reported synthesis methodology was altered to prepare MAC(Ali5)F. For the reaction 0.141 M pentafluoropropionic anhydride was added to the chitosan solution and stirred for 48 h at low speed (60 rpm) at room temperature (RT). The solution was then placed in a dialysis membrane (12,000-14,000 molecular weight cut-off Spectra/Por, Spectrum Labs, Rancho Dominguez, Calif.) and dialyzed against deionized water for 3 days with three changes per day, then lyophilized. This product was dissolved in 2 vol. % acetic acid/water, modified with methacrylic anhydride as described above, then freeze dried to yield MAC(Ali5)F.

1.2. Preparation of 2,3,4,5,6-Pentafluorobenzaldehyde Modified Methacrylamide Chitosan (MAC(Ar5)F)

First 0.04 M 2,3,4,5,6-pentafluorobenzaldehyde and 0.085 M sodium cyanoborohydride were mixed with 10 ml of 100% methanol. Then 10.58 g of 3% w/v chitosan/acetic acid solution was added and stirred at low speed (60 rpm) for 48 h at RT. This synthetic methodology was based on previously reported work. The reaction mixture was then dialyzed against deionized water for 3 days with three changes per day, then lyophilized. The lyophilized product containing chitosan was dissolved in 2 vol. % acetic acid/water and further reacted with methacrylic anhydride to yield MAC(Ar5)F.

1.3. Preparation of Pentadecafluorooctanoyl Chloride Modified Methacrylamide Chitosan (MAC(Ali15)F)

21.53 g of 3% w/v chitosan/acetic acid solution was mixed with 0.14 M pentadecafluorooctanoyl chloride. The reaction mixture was stirred at low speed (60 rpm) for 24 h at RT. The solution was then dialyzed against deionized water for 3 days with three changes per day, then lyophilized. This lyophilized fluorine-containing chitosan was further modified with methacrylic anhydride, as described above, to yield the product MAC(Ali15)F.

1.4. Preparation of Hydrogels and Gradient Hydrogels

For hydrogel formation MAC/MACF was first dissolved in ultrapure water (MilliQ Direct 8 system at 18 MX resistance, Millipore, Billerica, Mass.) at 2% w/v and then sterilized by autoclaving. Photoinitiator solution, 300 mg $ml^{-1}$ 1-hydroxycyclohexyl phenyl ketone (Sigma-Aldrich) in 1-vinyl-2-pyrrolidinone (Sigma-Aldrich,) was added to all solutions at 3 µl $g^{-1}$ (initiator/polymer solution). These solutions were thoroughly mixed and degassed (1 min, 3000 rpm, Speed Mixer DAC 150 FVZ, Hauschild Engineering, Hamm, Germany). Prior to polymerization samples were purged with excess $N_2$ to remove dissolved oxygen in the system. Solutions were transferred to a well plate for molding, and polymerization was achieved by exposure to UV light (365 nm) for 20 min.

The gradient hydrogel systems MAC/MAC(Ali5)F, MAC/MAC(Ar5)F and MAC/MAC(Ali15)F were prepared by continuous mixing using two variable syringe pumps (Cole Palmer, Court Vernon Hills, Ill.) that fed into a single outlet. The flow rates were adjusted to from 0 to 1 or from 1 to 0 ml $min^{-1}$ for two channels containing MAC and MACF, respectively. Gradients were created in a 20×40 mm rectangular culture plate by adjusting the flow of each constituent to ±10% every 4.0 mm as the outlet moved lengthwise across the well.

1.5. High Resolution 19F NMR Studies of MACFs

For all NMR quantifications chitosan, MAC and MACFs were dissolved in 2 vol. % deuterated acetic acid/$D_2O$. The existence of fluorine substitutions and confirmation of the MACF structures were attained by high resolution $^{19}$F NMR (pulsed Varian 400 MHz). The corresponding peak areas were utilized to calculate the degree of substitution, similar to the calculation of the degree of deacetylation using $^1$H NMR. Briefly, the degree of fluorination (DF) was calculated using the equation:

$$DF = \Sigma[1 + \{(I_{CF_n})/(I_{ref}/m_{ref})\}] \times 100\%$$

where $I_{CF_n}$ represents the integral intensity for each fluorine peak and m is the number of fluorines in each peak $I_{ref}$ represents integral intensity of a reference CF group. We employed trichlorofluoromethane ($CFCl_3$) as the reference, and $m_{ref}=1$.

1.6. Oxygen Uptake and Release Studies

Figure 3:
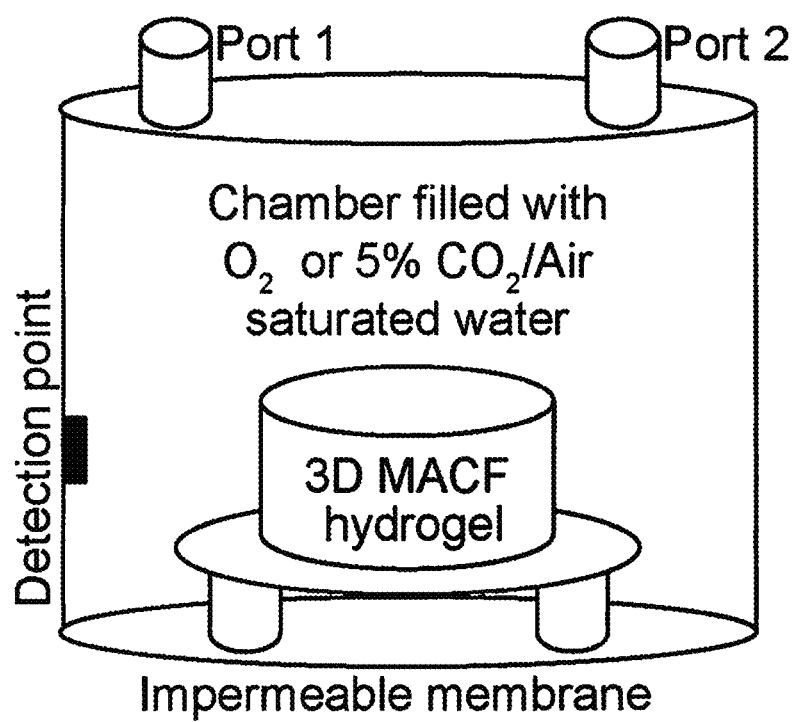
FIG. 3 provides a diagram of the oxygen uptake/release chamber. The ports are attached to tubing with valves to allow opening and closing. The detection point interfaces with an optical trace oxygen sensor connected to a computer for data collection.

The oxygen capacity of hydrogels (2% w/v formed in 6-well plates, 3.5 cm in diameter by 1 cm high) were measured indirectly by studying the oxygen uptake and release kinetics of the surrounding solution in a sealed chamber using a trace oxygen sensor (PreSens, Regensburg, Germany) connected to a computer running OxyView PST6-V5.41 for data collection (FIG. 3). During all uptake and release measurements the chamber was kept stagnant to create an environment similar to culture conditions or a wound dressing. Oxygen uptake was measured by first placing nitrogen purged polymerized hydrogels in oxygen-saturated ultrapure water (bubbled with pure $O_2$ at 258 mmHg for 15 min) in the sealed system and then measuring the amount of oxygen removed from the solution as it was adsorbed into the gel. $P_{O_2}$ of the solutions was continuously monitored at RT. $P_{O_2}$ data were acquired until the system reached equilibrium. Next, oxygen release was measured by changing the water in the system to oxygen-free 5% $CO_2$ ultrapure water (bubbled with 5% $CO_2$/95% air at 258 mm Hg for 15 min). $P_{O_2}$ oxygen release data were recorded until the closed system reached equilibrium. Repeated MACF hydrogel oxygen uptake and release responses were measured over three cycles to see if any changes occurred in hydrogel oxygen capacities or kinetics. These studies were designed to test whether MACF hydrogels could be utilized as reloadable oxygen delivery systems.

1.7. Hydrogel Rheology, Swelling and Scanning Electron Microscopy (SEM) Experiments To prepare samples for rheometry 10 ml of MAC/MACF solution was poured into a silicone mold and crosslinked as described above. The resulting hydrogel sheet was removed from the mold and equilibrated in phosphate-buffered saline (PBS) overnight. 8 mm diameter gels were cut out of the hydrogel sheet using a round biopsy punch and the mechanical properties of each hydrogel group were determined with a rheometer (Rheometric Scientific RFS-III, Piscataway, N.J.). Testing provided the storage modulus (G') and loss modulus (G"). G* was calculated, as it incorporates both the storage and loss modulus and is calculated directly by the rheometry software (TA Orchestrator) using the Pythagorean theorem:

$$G^* = \sqrt{(G')^2 + (G'')^2}$$

To estimate swelling ratios 500 μl of hydrogel were crosslinked for 20 min and freeze-dried. Next, their dry masses ($M_D$) were measured, followed by swelling of the previously dry hydrogel scaffolds in 1×PBS at 37° C. Swelling was complete in 24 h, such that no noticeable change in hydrogel mass was observed after this time point. Samples were carefully centrifuged on 50 μm cell strainers (1500 rpm) to remove any residual PBS. The mass after swelling ($M_S$) was determined when the mass no longer changed and the swelling ratio ($Q_M$) was calculated as:

$$Q_M = M_S/M_D$$

Samples were prepared for SEM by crosslinking hydrogels as described above, followed by freeze-drying. Samples were imaged using a FEI Quanta 200 environmental SEM (FEI, Hillsboro, Oreg.).

1.8. In Vitro Biocompatibility Testing

NIH-3T3 fibroblasts were cultured on MACF hydrogels to, first, confirm whether hydrogels incorporating PFCs were indeed nontoxic and, secondly, to determine whether PFCs provide any benefit in enhancing cell proliferation and viability. MACF and MAC hydrogels were created via photopolymerization in 48-well plates (11 mm diameter by 5 mm high), washed with PBS, then coated with 2.36 lg $ml^{-1}$ rat tail collagen for 5 h and finally washed with PBS. Collagen was added to provide cellular integrin attachments to maximize cell-material interactions. This concentration has been shown previously to be in the optimal range for this purpose. Fibroblasts were seeded onto the surface of MAC and all three MACF hydrogels at an a real cell density of $1 \times 10^4$ cells $cm^{-2}$. A chemically defined medium was used for all cell culture (Thera PEAK, Lonza, Basal, Switzerland) containing 1% penicillin/streptomycin (Life Technologies, Grand Island, N.Y.). The seeded hydrogels were placed in a cell culture incubator (5% CO2) maintained at 37° C. Half of the MAC and MACF hydrogels received oxygen loading via pure oxygen bubbling into the culture wells for 4 min. The MAC, MAC(Ali5)F and MAC(Ar5)F treatment groups that received initial oxygenation were resupplemented with oxygen for 4 min every 24 h. Hydrogels were cultured for a total of 4 days as preliminary testing revealed that fibroblasts neared confluence during that time on the surfaces with the most proliferation. At the end of the culture period the cultures were imaged with a bright field microscope (Olympus IX-81, Tokyo, Japan) and were prepared for 3-(4,5-dimethylthiazol-2-yl)-2,5-diphenyltetrazolium bromide (MMT) (Sigma-Aldrich) or Quant-iTPicoGreen (Life Technologies) total double-stranded DNA (dsDNA) assay.

1.9. MTT Analyses

The total metabolic activity of cells on each hydrogel after 4 days culture was estimated using the MTT assay. Briefly, a stock solution of MTT (5 mg $ml^{-1}$) was prepared in PBS

TABLE 1

| | Fluorinated methacrylamide chitosan | | | |
|---|---|---|---|---|
| Name | Abbreviation | Degree of PFC substitution per unit monmer (%) | $O_2$ adsorption capacity (mmHg) | $O_2$ adsorption capacity (mmHg) |
| Methacrylic anhydride modified chitosan | MAC | 0 | 0 | 0 |
| Pentafluoropropionic anhydride modified methacrylamide chitosan | MAC(Ali5)F | 37-40 | 47.34 ± 1.08 | 0.88 ± 0.21 |
| 2,3,4,5,6-Pentafluorobenzaldehyde modified methacrylamide chitosan | MAC(Ar5)F | 40-43 | 89.10 ± 2.11 | 3.79 ± 0.55 |
| Pentadecafluorooctanoyl chloride modified methacrylamide chitosan | MAC(Ali15)F | 39-43 | 134.20 ± 6.07 | 0.81 ± 0.37 | and filter sterilized through a 0.2 lm filter, then added to each well. The cell-seeded hydrogels and unseeded controls were incubated in chemically defined medium (medium with no phenol red) for 5 h in a 5% CO2 incubator at 37 C to allow the assay to develop the purple formazan salt. Next, the medium was carefully removed and the formazan salt was dissolved by adding 100 ll of DMSO and incubating for 15 min. Absorbance of the solution was measured with a microplate reader (Infinite M200, Tecan, Grödig, Austria) at 570 and 690 nm. The results are reported as fold change in metabolic activity compared with unoxygenated cell-seeded MAC controls after correction using the unseeded controls. A similar protocol was followed to determine the metabolic activity of cells across gradient hydrogels. Each gradient hydrogel was carefully cut into eight 5×20 mm strips across the entire 40 mm length of the gel and each strip was cut into three equal pieces. Next, each piece was transferred to a separate well of a 24-well plate and the MTT assay was performed as described above. Results were reported as fold change in metabolic activity compared with the 100% MAC region of the unoxygenated gradient hydrogels.

1.10. PicoGreen Total dsDNA Analyses

Total cell number was quantified using the Quant-iT PicoGreen dsDNA kit. A 1×TE working solution (10 mM Tris-HCl, 1 mM EDTA, pH 7.5) was prepared by diluting the concentrated buffer 20-fold with sterile DNase-free ultrapure water. A working solution of Quant-iTPicoGreen reagent was prepared by making a 200-fold dilution of concentrated DMSO solution in TE and protected from light. The standard curve was prepared using the supplied λ-DNA standard. The working solution was added to each well and incubated for 5 min at RT protected from light. Fluorescence was measured with a microplate reader (Infinite M200) using an excitation of 480 mm and emission of 520 mm. Total dsDNA concentration was determined by correlation with a standard curve after correction using the unseeded controls and converted to total cell number using a conversion factor of 6.6 pg DNA per cell.

1.11. Statistics

All statistical analyses were performed using JMP 9 (SAS Institute, Cary, N.C.). ANOVA with Tukey's post hoc analysis was performed to detect significant differences between groups. An α level of 0.05 was used to determine significance between groups. Capital letters are used to denote significance when multiple significant differences were detected. Different letters imply that a significant difference exists between groups. Data are reported as mean±standard deviation (SD).

2. Results 2.1. Synthesis and Characterization of MACFs

Figure 4:
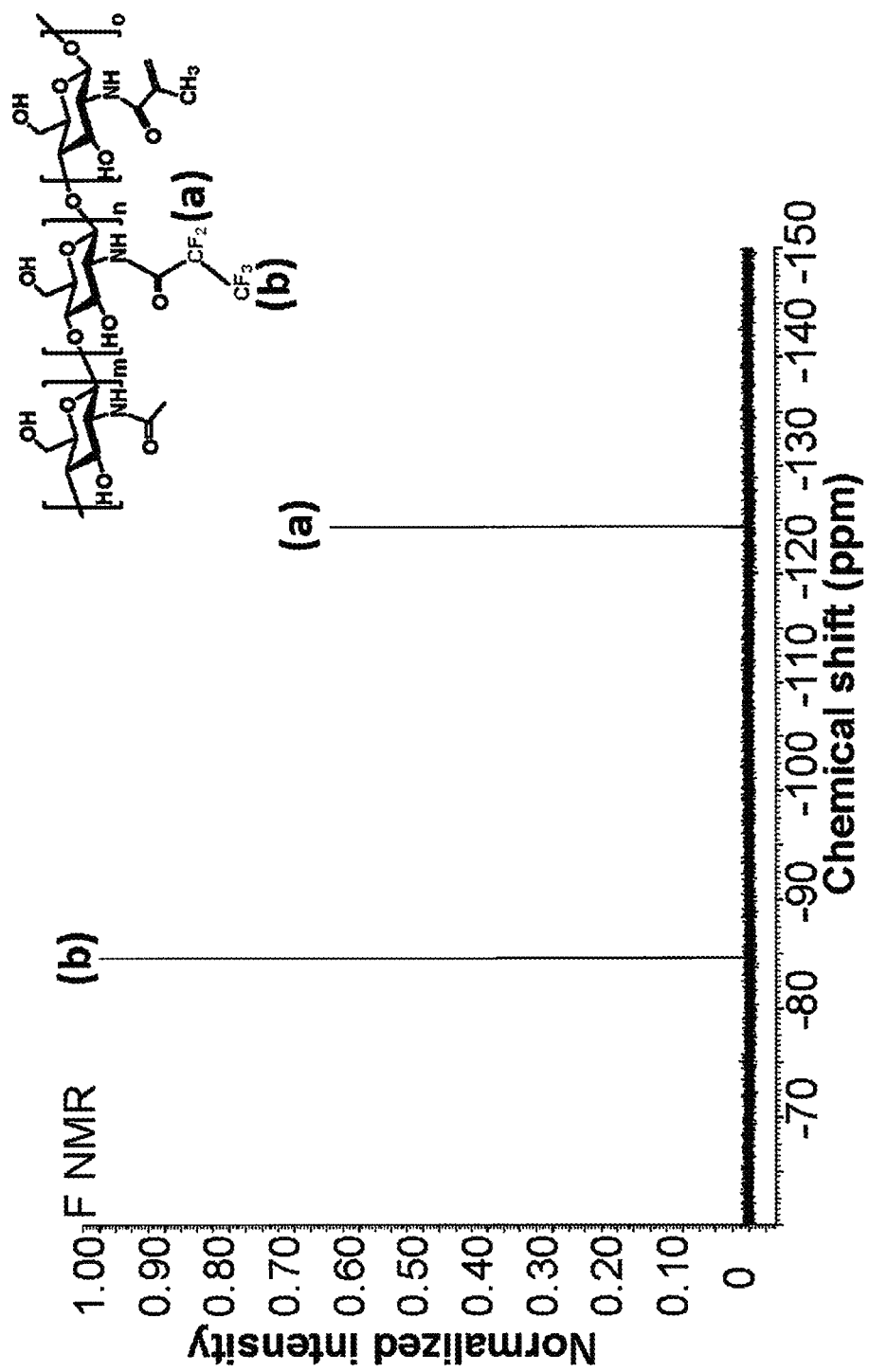
FIG. 4 provides a high resolution 19F NMR spectra for one or more embodiments, MAC(Ali5)F, confirming the fluorine substitutions.
Figure 5:
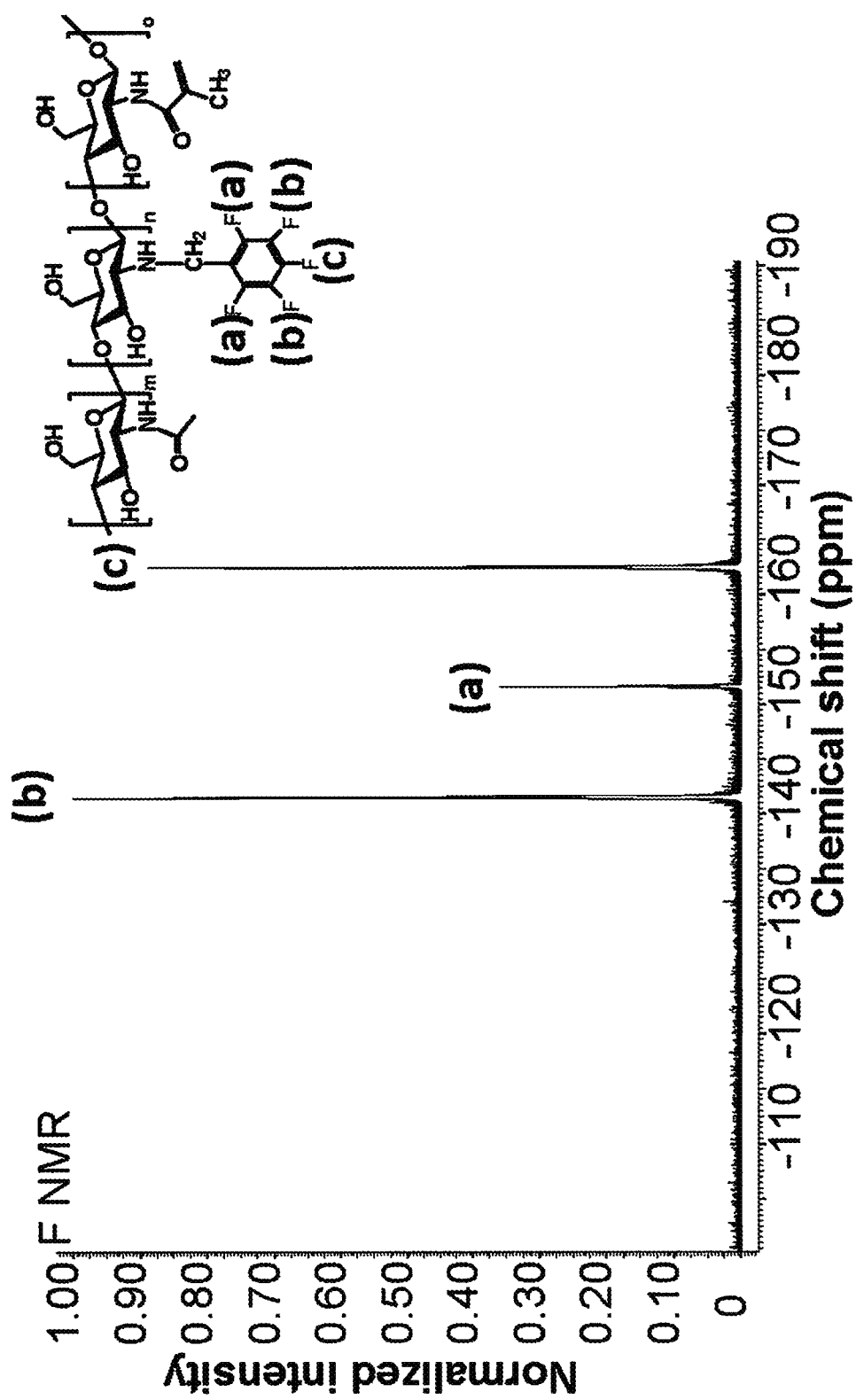
FIG. 5 provides a high resolution 19F NMR spectra for one or more embodiments, MAC(Ar5F), confirming the fluorine substitutions.
Figure 6:
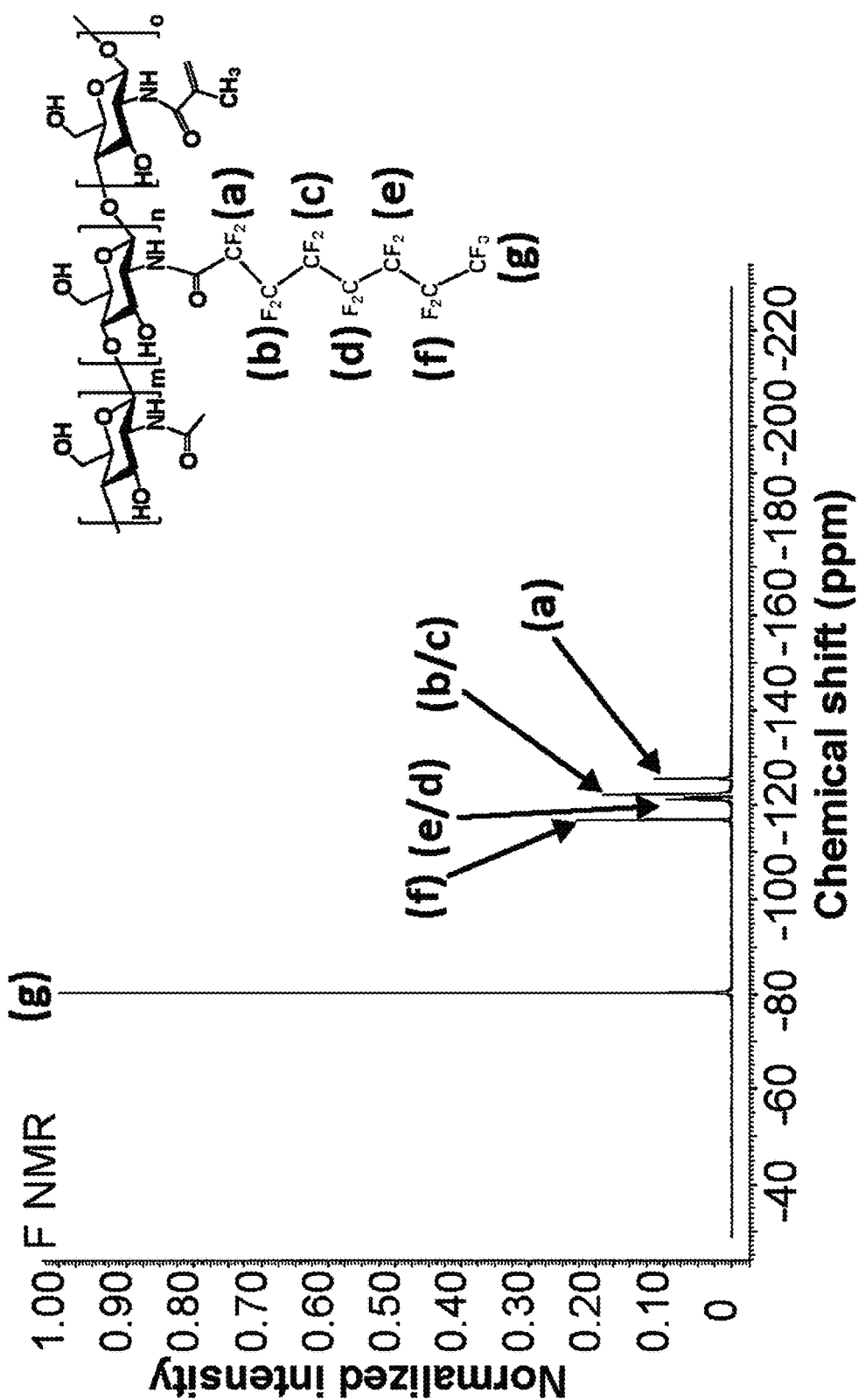
FIG. 6 provides a high resolution 19F NMR spectra for one or more embodiments, MAC(Ali15)F, confirming the fluorine substitutions.

Table 1 summarizes the MACF materials that were synthesized in these studies. High resolution $^{19}$F NMR spectroscopy (FIG. 4 to FIG. 6) revealed that the degree of PFC substitution lies in the range 37-43% for all three MACFs. During PFC conjugation each MACF reaction mixture remained homogeneously mixed at low viscosity throughout the period of the reaction. Thus it is assumed that the PFC ligands were uniformly distributed throughout the polymer network. This was confirmed by the $^{19}$F NMR spectrum, that indicated the absence of additional peaks (FIG. 4 to FIG. 6).

2.2. MACF Oxygen Uptake and Release Behavior

We utilized our custom built device (FIG. 3) to determine whether PFC addition indeed conferred the ability to takeup oxygen from a high oxygen tension solution then release oxygen into a low oxygen tension aqueous environment. Static oxygen uptake and release by MAC(Ali5)F, MAC(Ar5)F, MAC(Ali15)F and unmodified MAC hydrogels are presented in FIG. 7 to FIG. 9, and FIG. 10. MAC alone had no fluorine substitution and thus no oxygen uptake. MAC(Ali5)F, which contains the least number of fluorine substitutions, showed an uptake capacity of 32.31±1.2 mm Hg. Interestingly MAC(Ar5)F, a material with a similar number of fluorines in an aromatic PFC, was able to take up 112.5±1.8 mm Hg oxygen. Our most fluorine substituted material, MAC(Ali15)F, showed an uptake capacity of 137.50±3.07 mm Hg. All equilibrium oxygen uptake capacities were significantly different from one another by one-factor ANOVA (P<0.0001).

Figure 11:
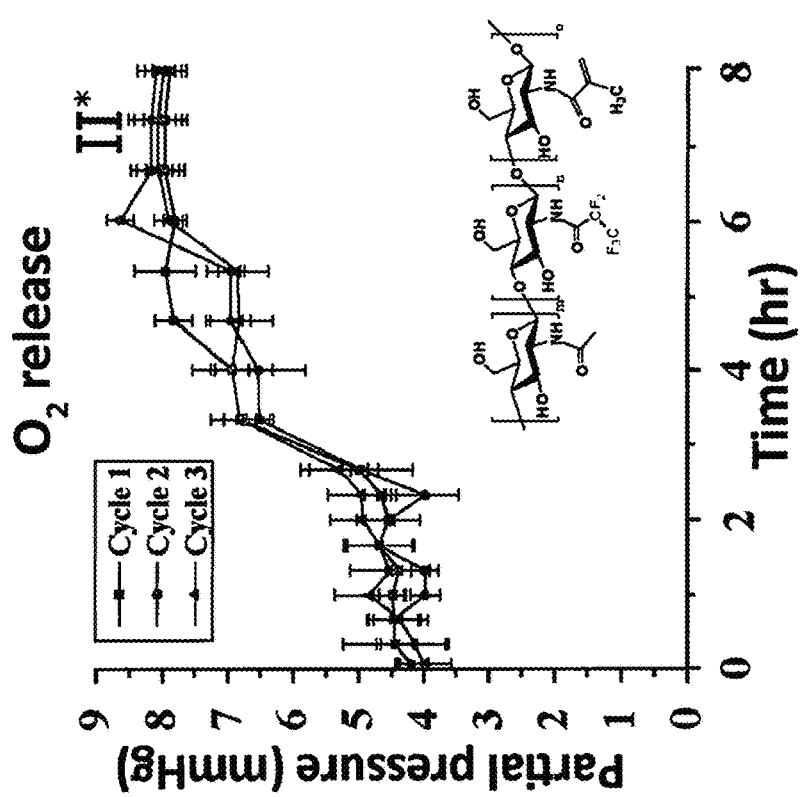
FIG. 11 provides three repeated oxygen uptake and release cycles for one or more embodiments, MAC(Ali5)F showing uptake (II) and the corresponding release(II*) at RT. Each data point represents n=3, mean±SD.
Figure 11:
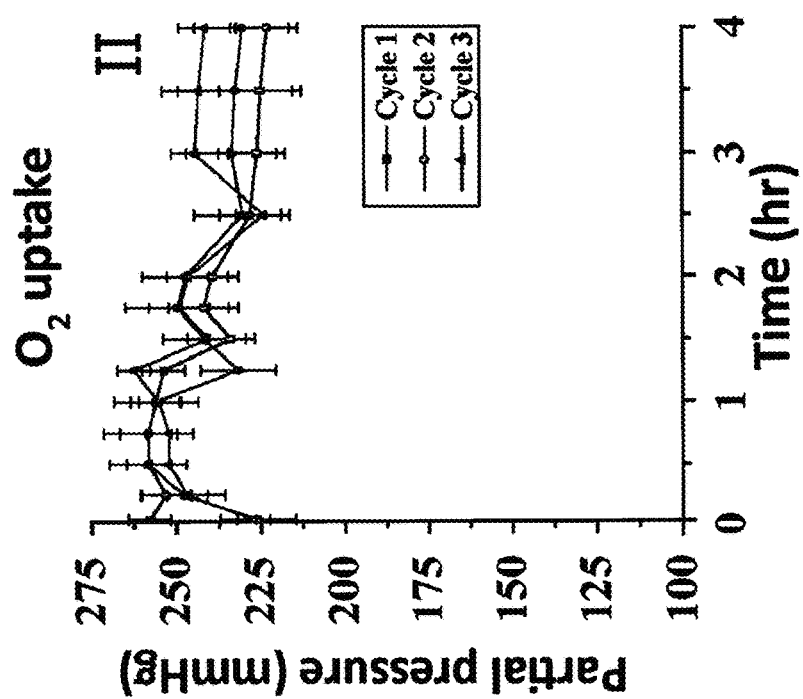
Figure 12:
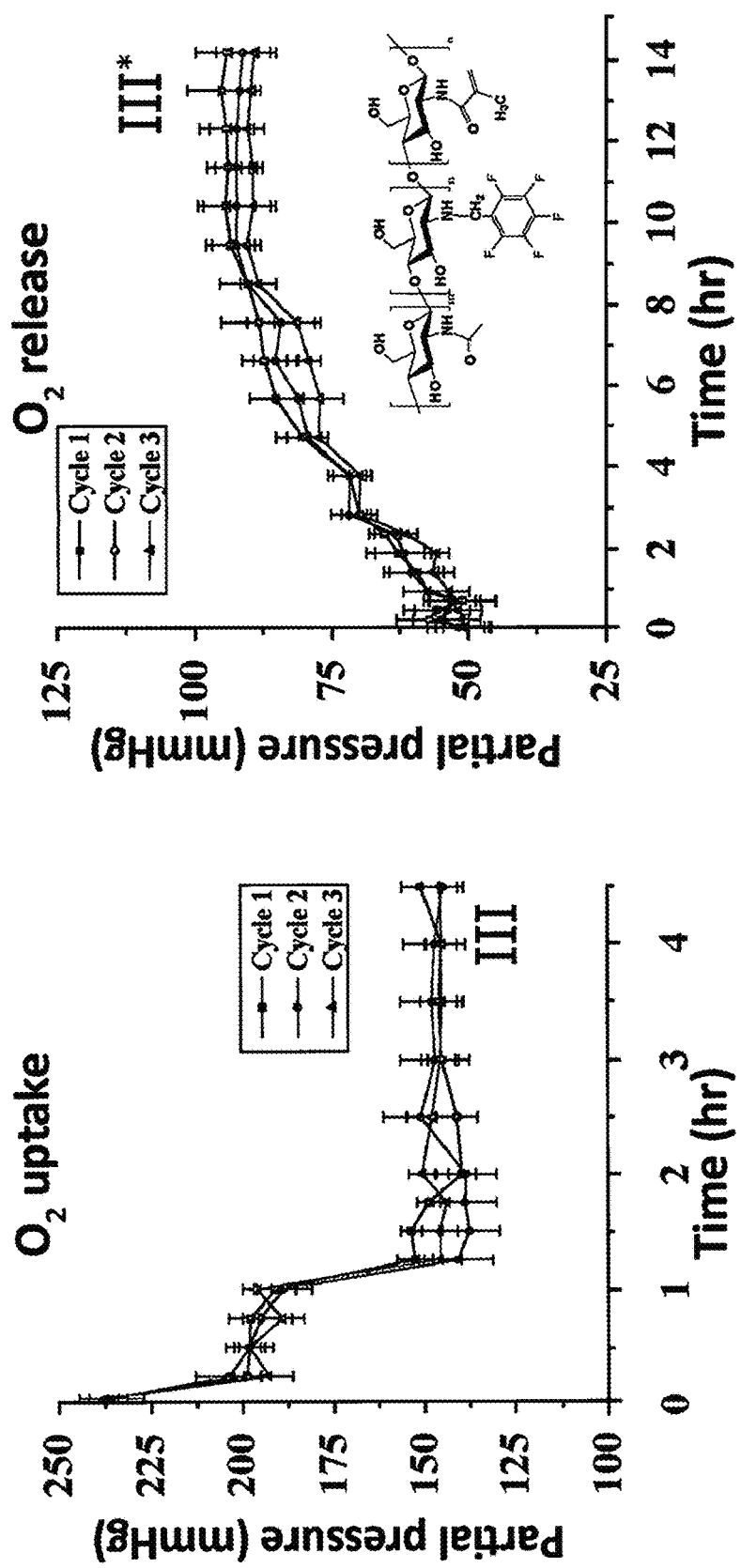
FIG. 12 provides three repeated oxygen uptake and release cycles for one or more embodiments, MAC(Ar5)F, showing uptake (III) and the corresponding release(III*) at RT. Each data point represents n=3, mean±SD.
Figure 13:
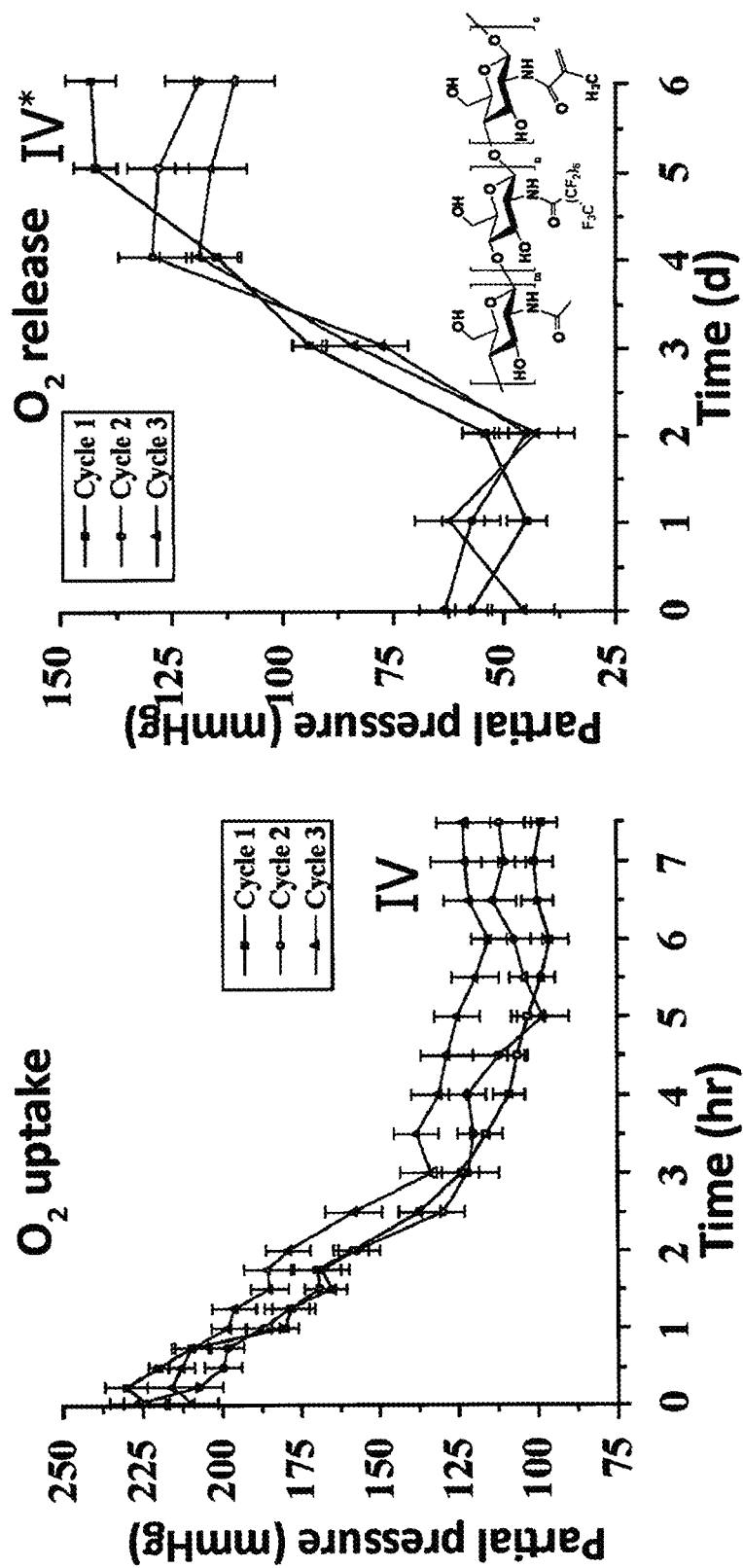
FIG. 13 provides three repeated oxygen uptake and release cycles for one or more embodiments, MAC(Ali15)F, showing uptake (IV) and the corresponding release(IV*) at RT. Each data point represents n=3, mean±SD.

Oxygen release from our materials showed that MAC(Ali5)F hydrogels released 8.21±0.80 mm Hg, MAC(Ar5)F released 89.10±2.45 mm Hg and MAC(Ali15)F released 134.20±3.73 mm Hg oxygen under static conditions. All equilibrium release $P_{O_2}$ data are significantly different from one another by one-factor ANOVA (P<0.0001). The least fluorinated material, MAC(Ali5)F, showed equilibrium release within 3.5 h. MAC(Ar5)F and MAC(Ali15)F demonstrated equilibrium oxygen release within 13.2 and 120 h (5 days) respectively. To understand whether our MACF hydrogel systems could be used multiple times we repeated the uptake and release procedures on samples from each MACF group (FIG. 11 to FIG. 13). Our investigation indicated three successful regeneration cycles with an $O_2$ capacity loss of 2.5±1.5% for all materials combined.

2.3. MACF Rheological Properties, Swelling Properties and SEM

The rheology and swelling results and the accompanying statistical analyses are summarized in Table 2. G' was greater than G" throughout the frequency range of rheological testing for all four materials tested, indicating gel properties. MAC resulted in the stiffest hydrogels, whereas MAC(Ar5)F resulted in the softest (P<0.0001). Generally speaking for MACFs the greater the number of fluorines per addition the stiffer the hydrogel. Swelling of the fluorinated hydrogels also demonstrated a correlation between the number of fluorines per addition and the swelling ratio. Statistical analysis showed that MAC(Ali5)F had a significantly higher swelling ratio than the other hydrogels tested (P<0.0001).

SEM images showed that MAC was very ordered, coinciding with the fact that it has no interacting side chains. MAC(Ali5)F showed a disordered and porous surface. This disordered composition was also seen for MAC(Ali15)F. A difference in polymer density was seen in both the aliphatic MACFs. MAC(Ali15)F showed a random structure and was not very porous. Finally, MAC(Ar5)F was very porous and the most ordered of the MACFs. The pores were large compared with the other MACFs, and although the cross-linked structure was not as ordered as pure MAC, it still showed some organization, unlike the disordered structure of the aliphatic MACFs.

TABLE 2

Summary of the rheology and swelling results

| Material | G*(Pa) | Statistic | Swelling ratio | Statistic |
|---|---|---|---|---|
| MAC | 2451.9 ± 604.7 | A | 11.3 ± 0.3 | B |
| MAC(Ali5)F | 1497.2 ± 508.7 | B C | 14.6 ± 0.6 | A |
| MAC(Ar5)F | 963.4 ± 79.7 | C | 11.1 ± 0.6 | B |
| MAC(Ali15)F | 2105.1 ± 877.4 | A B | 10.6 ± 0.2 | B |

Rheomtery data n = 10, swelling data n = 5, means ± SD.
Different letters are significantly different from one another by multi-factor ANOVA (P < 0.0001).

2.4. Cellular Responses to MACFs

Microscopy images from day 4 show that fibroblasts prefer MACFs with more fluorines per PFC substitution.

Figure 14A:
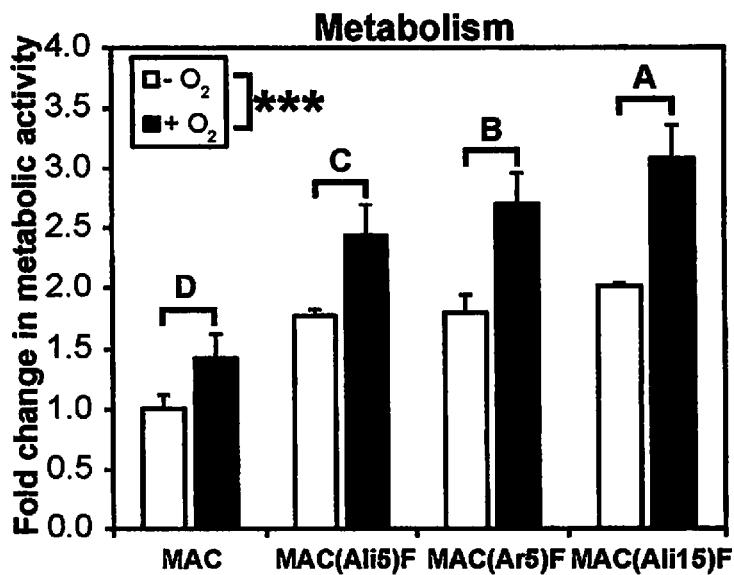
FIG. 14A provides MTT metabolic assays of fibroblast cell cultures for one or more embodiments, while FIG. 14B provides PicoGreen total dsDNA assays of fibroblast cell cultures for one or more embodiments. MAC(Ali5)F, MAC(Ar5)F and MAC(Ali15)F without oxygen reloading (−$O_2$) or with reloading (+$O_2$) at 4 min day$^{-1}$, except for MAC(Ali15)F, which received 4 min 4 days$^{-1}$. Initially 9.5×$10^3$ cells were seeded (dotted line) onto the hydrogels and cultured under normal conditions (5% CO2, 37 C) for 4 days. *Significant difference at P<0.0001; significant difference at P=0.007). Letters above the grouping brackets are significantly different from one another by multi-factor ANOVA (P<0.0001). All data n=3, means±SD.
Figure 14B:
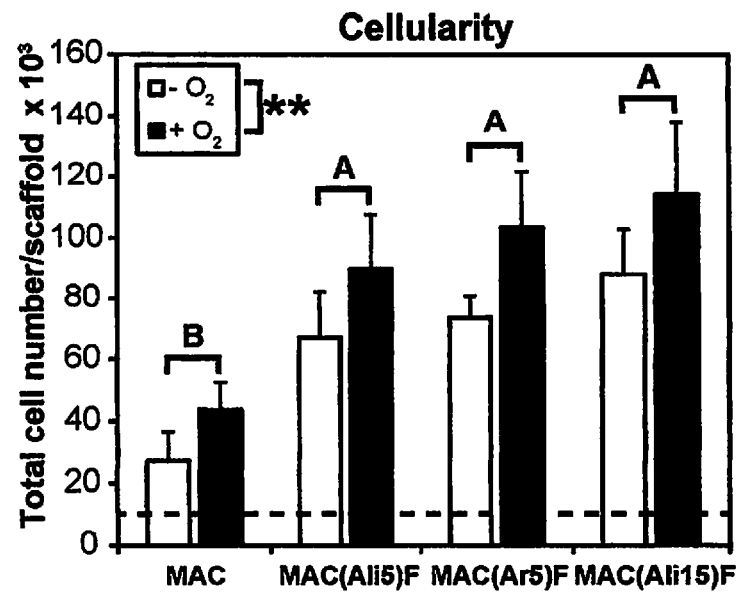

Metabolic rates and total number of cells supported by each MACF hydrogel type are presented in FIG. 14. Three-factor ANOVA (material type, $O_2$ regeneration, material type×$O_2$ regeneration, all with significant leverage P<0.0001) was used to analyze metabolic activity. Two-factor ANOVA (material type, $O_2$ regeneration, all with significant leverage P<0.0001) was used to analyze the total cell number data. Metabolic activity (FIG. 14A) was enhanced by material type/number of fluorines per addition (P<0.0001) as well as $O_2$ reloading at the specified interval (P<0.0001). Total cell number supported by each hydrogel (FIG. 14B) was significant for all MACFs compared with MAC controls (P<0.0001) and $O_2$ reloading was significant (P=0.007).

3.5. Cellular Responses to MACF Gradients

To demonstrate how fluorine substitution and amount can control oxygen release from a biomaterial hydrogel at a spatial level we developed a series of gradient gel systems. Three-factor ANOVA (position, $O_2$ regeneration, position× O2 regeneration, all with significant leverage P<0.0001) was used to analyze metabolic activity on the gradients. Our studies indicate that cell metabolic activity increases as the percentage of MACF increases (FIG. 15 to FIG. 17) (P<0.0001). This response was most evident in MAC/MAC (Ali15)F gradients, in which more PFCs were incorporated into the right-hand side of the hydrogel (FIG. 17). These results further indicate that oxygen-treated gradient systems have greater metabolic activity compared with gradient gels not given oxygen during the culture period (FIG. 16 and FIG. 17) (P<0.0001).

3. Discussion

PFC modification of MAC creates an injectable and moldable system that can be formed into hydrogels with established techniques. Immobilization of PFCs on a crosslinked biomaterial provides a stable support structure to facilitate oxygen delivery, which is difficult to achieve in vivo with colloidal PFC suspensions. Additionally, we demonstrated that PFC modification can be changed to modify the oxygen uptake and release capacity and kinetics.

Chitosan is a naturally abundant polysaccharide containing many reactive sites (free amines and hydroxyl groups) to covalently incorporate various small molecules such as PFCs and many chitosan-based materials have been reported in diverse areas with numerous applications. Chitosan on its own has been intensely studied in dermal wound healing, as it is hemostatic and antibacterial. We have previously studied a modified photopolymerizable chitosan MAC and its utility in tissue engineering, and the results of this study build upon this work. MAC is soluble in aqueous buffers and is typically formed into hydrogels. Fluorinated chitosan and similar fluorine-derivatized materials have been previously reported, however, the oxygen uptake and release properties of these materials have not been well characterized or widely studied with regard to their ability to support cells or in wound healing applications.

Previous investigations of fluorinated chitosan systems have demonstrated that fluorine substitution is optimal in the range 40-45% to support cells, and undesirable effects are seen above this substitution range. Our substitutions fall within this ideal range (Table 1) and we assumed that the PFC ligands were uniformly distributed throughout the polymer network, since the reactions were continuously stirred without noticeable precipitate. Additionally, the reaction conditions were performed in dilute acetic acid with a pH that favored only the reaction of primary amines over any other potential reactive groups in chitosan. A uniform fluorine distribution is crucial to facilitate even and spatially controlled oxygen uptake and release, especially for guiding cellular responses.

The results of the oxygen uptake and release studies (FIG. 7 to FIG. 10) indicate the importance of selecting the appropriate PFC modification in order to tune the capacity and total release time. Uptake occurred quickly, reaching $P_{O_2}$ equilibrium in 2-6 h, followed by slower release to the surrounding environment (5% $CO_2$/95% air) within 12-120 h, at a $P_{O_2}$ of 1-25 mm Hg $h^{-1}$. This shows that our approach allows outstanding system tuning, which is important for various applications in wound healing and tissue regeneration.

Figure 7:
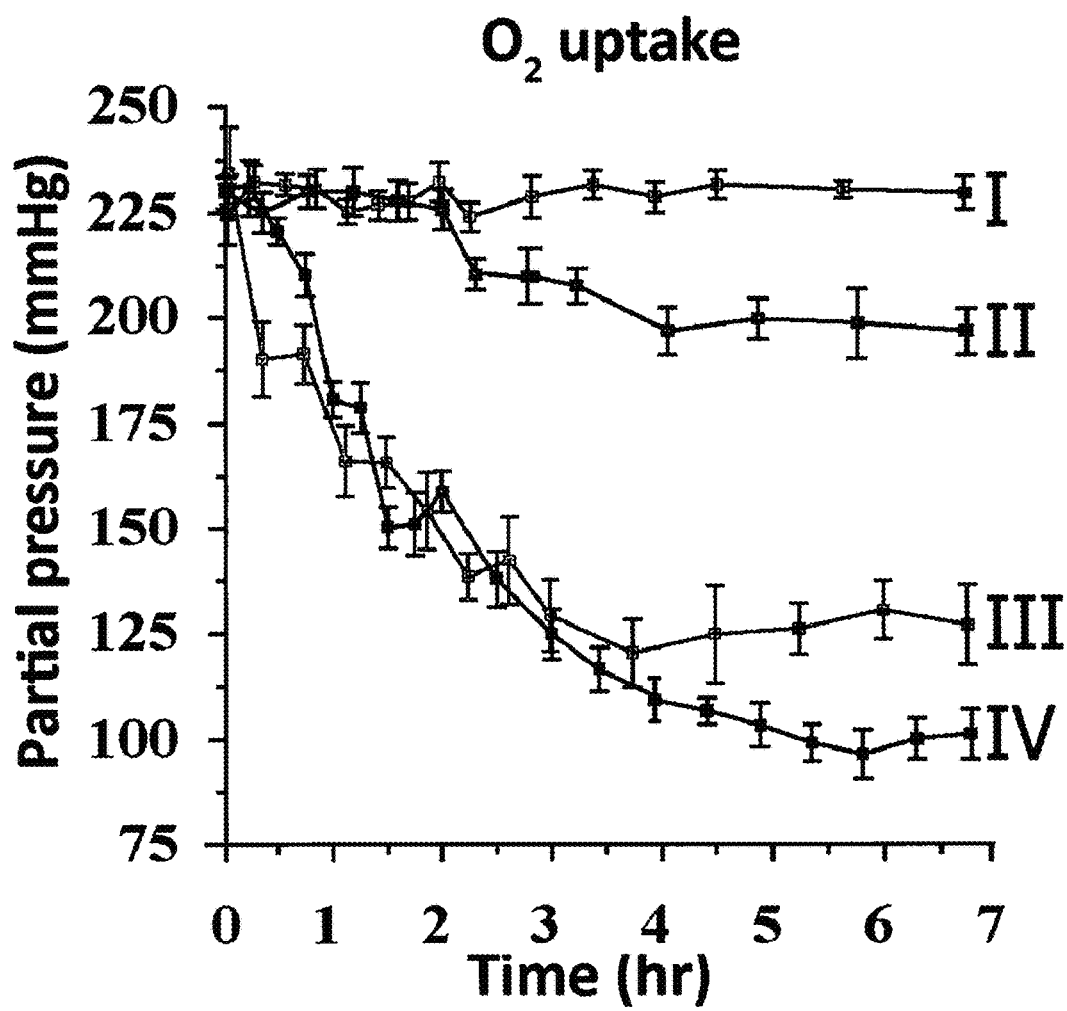
FIG. 7 provides oxygen uptake, of a comparison and one or more embodiments, MAC, MAC(Ali5)F, MAC(Ar5)F and MAC(Ali15)F (I, II, III and IV) at RT in 5% $CO_2$/95% air under static conditions at RT. Hydrogels were composed of 2 wt. % MAC or MACF, with hydrogel volumes of 9.6 $cm^3$. Each data point represents n=3, mean±SD.
Figure 8:
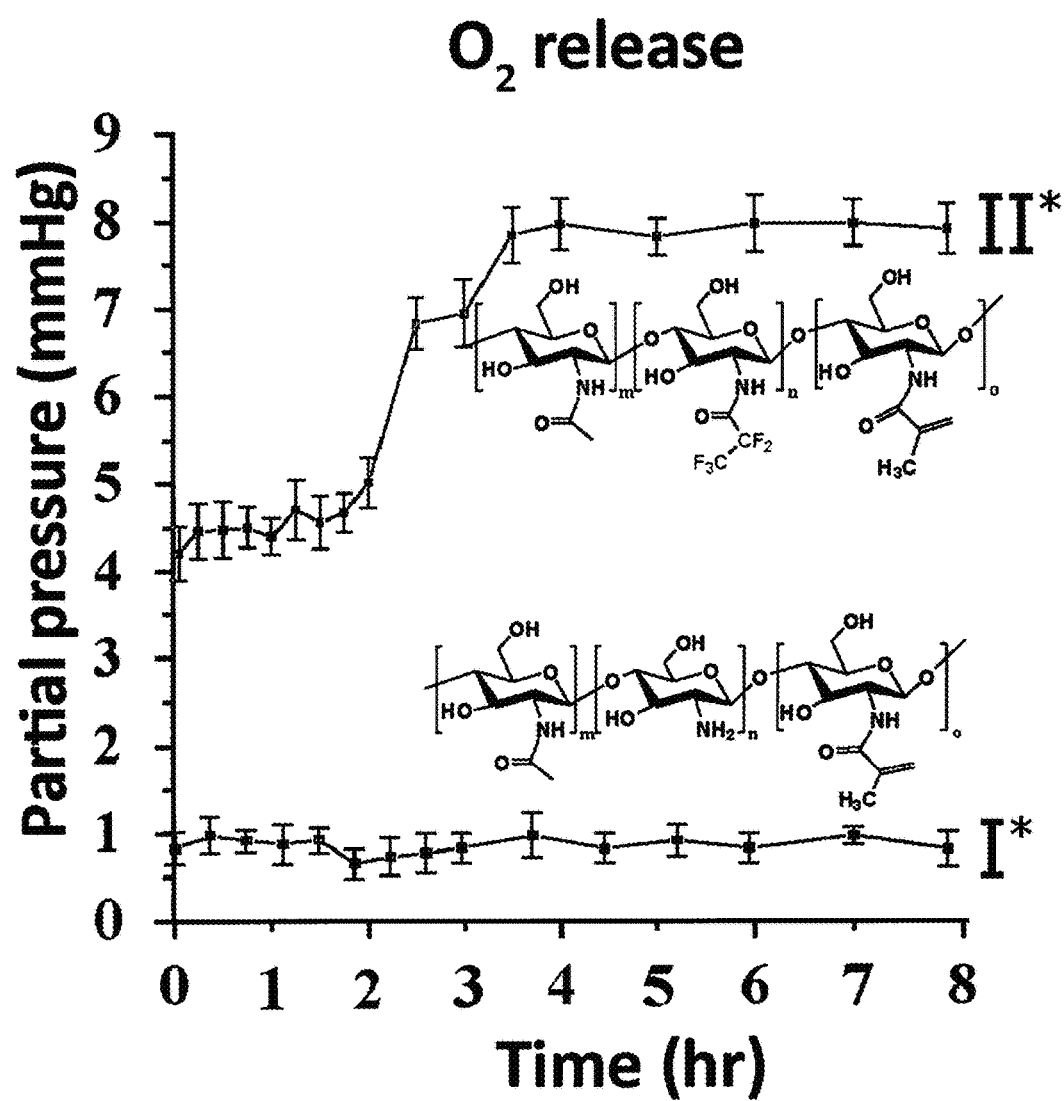
FIG. 8 provides Oxygen desorption, of a comparison and one or more embodiments, MAC, MAC(Ali5)F, (I* and II*) at RT in 5% $CO_2$/95% air under static conditions at RT. Hydrogels were composed of 2 wt. % MAC or MACF, with hydrogel volumes of 9.6 $cm^3$. Each data point represents n=3, mean±SD.
Figure 9:
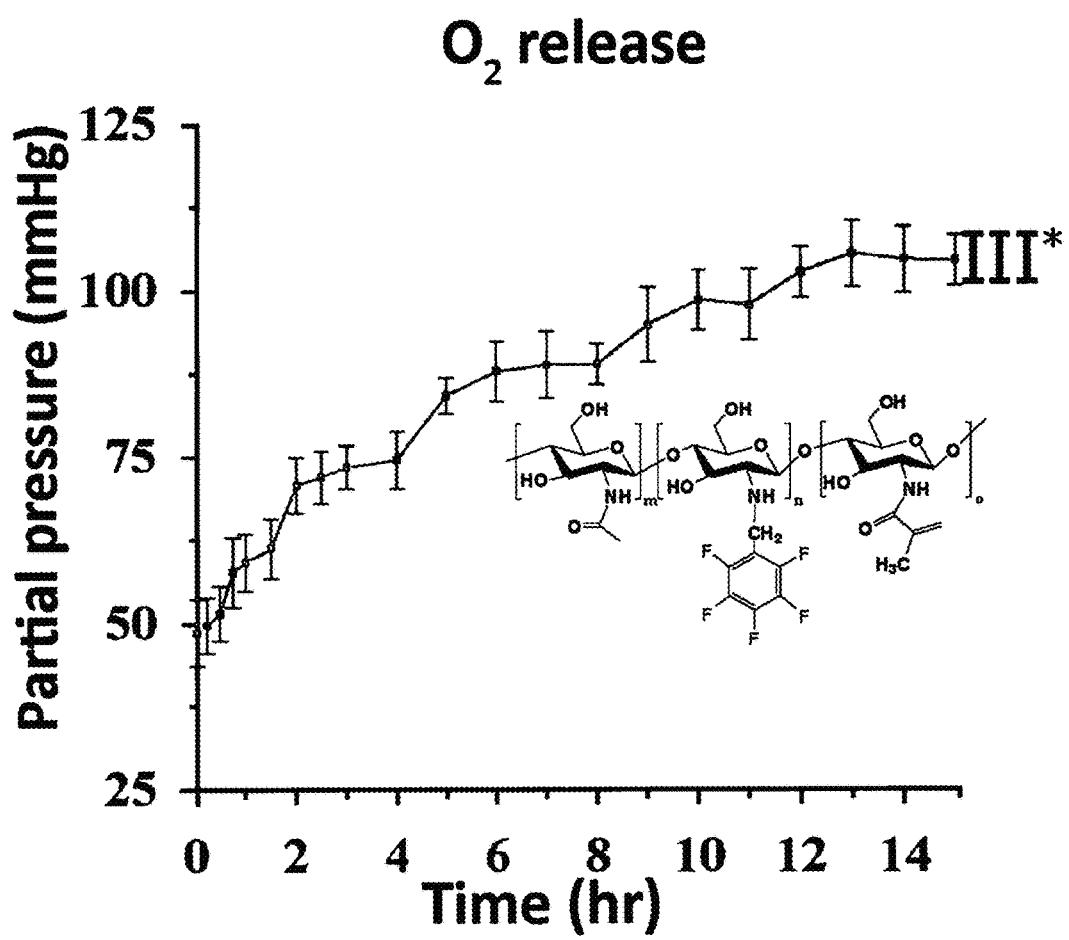
FIG. 9 provides oxygen desorption, of one or more embodiments, MAC(Ar5)F (III*) at RT in 5% $CO_2$/95% air under static conditions at RT. Hydrogels were composed of 2 wt. % MAC, with hydrogel volumes of 9.6 $cm^3$. Each data point represents n=3, mean±SD.
Figure 10:
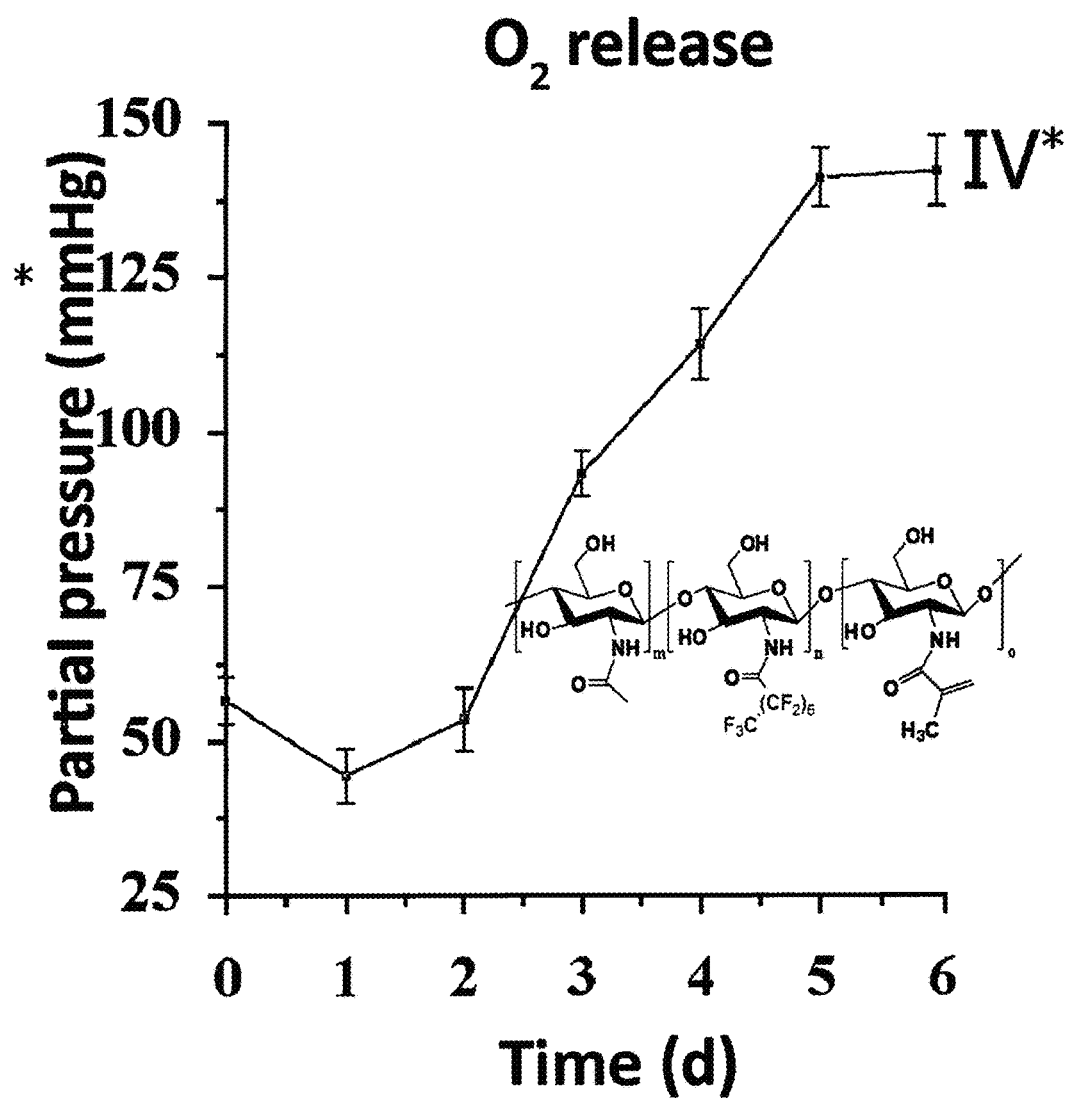
FIG. 10 provides oxygen desorption, of one or more embodiments, MAC(Ali5)F (IIII*) at RT in 5% $CO_2$/95% air under static conditions at RT. Hydrogels were composed of 2 wt. % MAC, with hydrogel volumes of 9.6 $cm^3$. Each data point represents n=3, mean±SD.

The uptake and release behavior demonstrated a direct correlation with the type of ligand and amount of fluorine attached to the PFC molecule. Interestingly, the motional dynamics of the bonded ligands play a significant role in this process. This helps to explain the drastic differences in oxygen uptake and release when comparing MAC(Ar5)F and MAC(Ali5)F (FIG. 7 to FIG. 10). MAC(Ar5)F demonstrated even greater dissociation rates than MAC(Ali15)F and showed a notable lag, like MAC(Ali5)F and MAC (Ali15)F (FIG. 8 to FIG. 10). MAC(Ar5)F contains fluorinated aromatic rings that have comparatively restricted mobility compared with linear PFC chains. Thus the aromatic PFC modifications orient all fluorine atoms in a single plane providing high accessibility to oxygen. This is in direct contrast to MAC(Ali5)F, which consists of the same number of fluorines per PFC modification, however, these fluorinated ligands are highly mobile, resulting in less stable F—$O_2$ interactions and thus a reduced oxygen uptake capacity and accelerated release (FIG. 7 and FIG. 8). MAC (Ali15)F contains long fluorinated carbon chains providing even less accessibility to oxygen compared with MAC (Ar5)F due to even more mobile PFC ligands. However, MAC(Ali15)F contains more fluorines per substitution and, therefore, the system requires a longer time to reach both its uptake and release equilibrium points (FIG. 4).

Our static $P_{O_2}$ uptake and release measurements demonstrated that the desorption of oxygen is always less than the adsorption for all gel systems (FIGS. 7 to 13). This confirms that a certain percentage of oxygen remains inside the hydrogel once equilibrium release occurs. This is advantageous during cell culture in that surplus oxygen is always available for cell proliferation. Dermal fibroblasts have previously been shown to be sensitive to oxygen levels and show enhanced metabolic activity at $P_{O_2}$ exceeding 50 mm Hg. Additionally, release studies showed that our systems exhibit a sigmoidal oxygen dissociation curve, which is similar to the dissociation of oxygen in blood. PFC emulsion systems do not show this behavior, and provide linear release. The similar oxygen transport characteristics of our MACF system to those of hemoglobin may be preferred by cells, as selected by evolution.

The results of our uptake/release cycling experiments (FIG. 11 to FIG. 13) were vital to confirm that our materials performed similarly when regenerated. The results in FIG. 11 to FIG. 13 further demonstrate that our hydrogels could be used for longer periods of time and still retain similar oxygen delivery characteristics. This is important, since in our cell experiments the materials were reloaded up to four times (FIGS. 14 to 17). This work further indicates that MACFs could be deployed to enhance both long- and short-term wound healing treatments. Increasing wound oxygenation levels by $P_{O_2}$ increments of only 5-10 mm Hg shows significant healing benefits for both acute and chronic wounds.

Although our swelling and rheology results (Table 1) do not completely parallel one another, important trends exist in both studies. Rheology showed that MAC hydrogels were stiffest, suggesting that the least substituted chitosan polymer chains allowed less inhibition during free-radical polymerization and thus greater crosslinking. Substituting PFCs on the MAC chains decreased chemical crosslinking, resulting in less stiff hydrogels. Another important behavior was observed on studying the results for the PFC-substituted materials (MACFs), demonstrating that longer more mobile PFCs gave elasticity to the hydrogel. Based on this concept, we believe that the fact that MAC(Ali15)F was the stiffest of the PFC-substituted hydrogels makes sense, because although additional substitution on MAC decreases chemical crosslinking, the longer the chain the greater the intermolecular forces present. It then follows that MAC(Ali5)F is the next in stiffness, as it is similar in composition but with shorter PFC chains. MAC(Ar5)F is the softest hydrogel, indicating low intermolecular forces due to the stability and nature of the aromatic molecules.

Swelling of the fluorinated hydrogels showed that MAC (Ali5)F swelled the most, and significantly more than the other three hydrogels which showed similar results to one another. One might expect that the swelling results would be inversely correlated with the reported G* values, however, as was observed by rheometry, there are interesting interactions that occur because of how the PFC additions differently disrupt free radical-initiated crosslinking, as well as how each PFC substitution adds varied intermolecular interactions to the hydrogels. We expected that a greater number of fluorines per substitution would lead to stiffer gels and less swelling. Likewise, fewer fluorines would lead to softer gels due to steric hindrance and, therefore, should lead to greater swelling, as was seen with MAC(Ali5)F. However, MAC (Ar5)F does not entirely conform to this behavior. We believe that this is because the aromatic rings in MAC (Ar5)F show a strong enough association to affect swelling, but not strong enough to affect the mechanical properties as measured by rheometry. Thus MAC(Ar5)F has an ordered structure, but not to the degree of MAC. MAC(Ar5)F does not allow a greater degree of swelling and is simultaneously a softer material. More tests should be performed in the future to better understand how PFC modifications change hydrogel properties at the molecular level.

Figure 15:
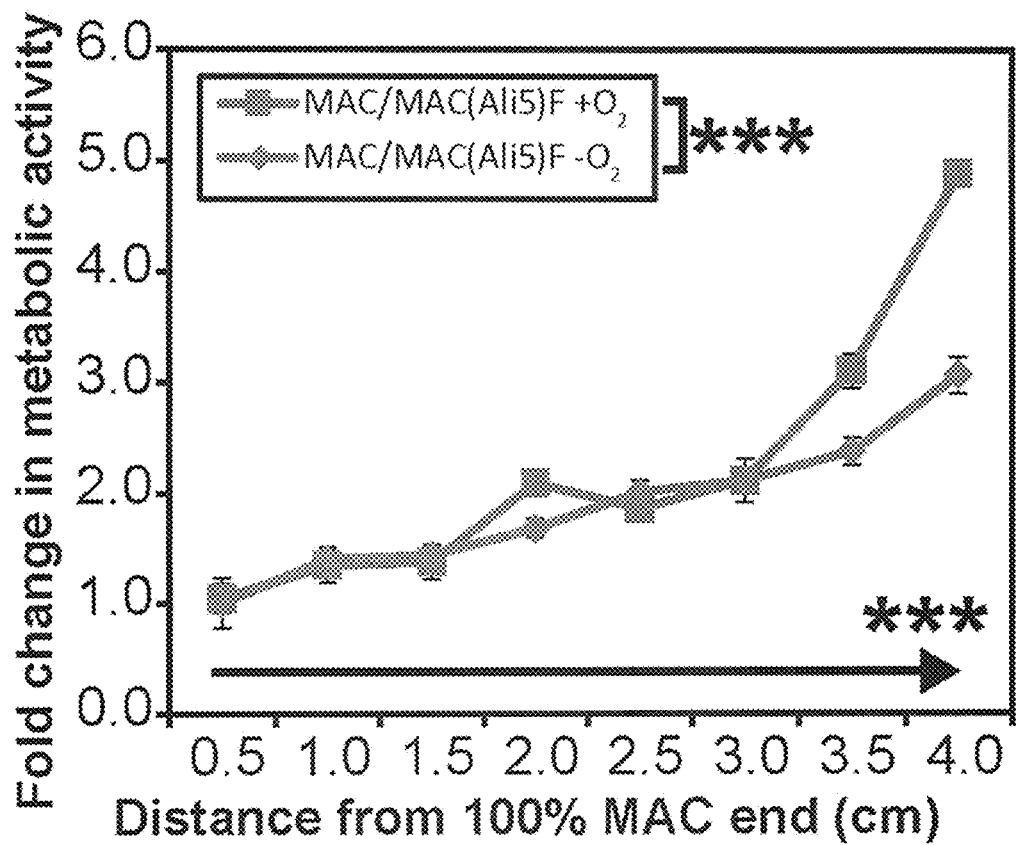
FIG. 15 provides a graph of one or more embodiments, MAC/MAC(Ali5)F, showing enhanced metabolism with more fluorine and supplemental oxygen. The results are reported as fold change compared with 100% MAC-$O_2$ regions. ***Significant difference by three-factor ANOVA (P<0.0001). All data n=3, means±SD.
Figure 16:
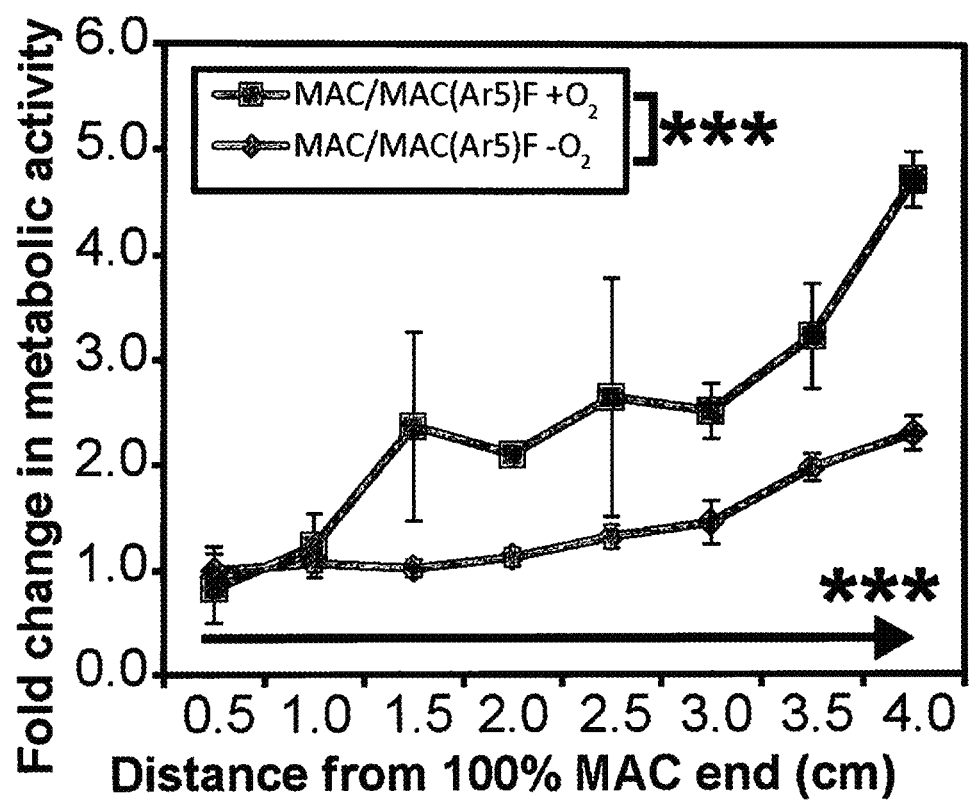
FIG. 16 provides a graph of one or more embodiments, MAC/MAC(Ar5)F, showing enhanced metabolism with more fluorine and supplemental oxygen. The results are reported as fold change compared with 100% MAC-$O_2$ regions. ***Significant difference by three-factor ANOVA (P<0.0001). All data n=3, means±SD.
Figure 17:
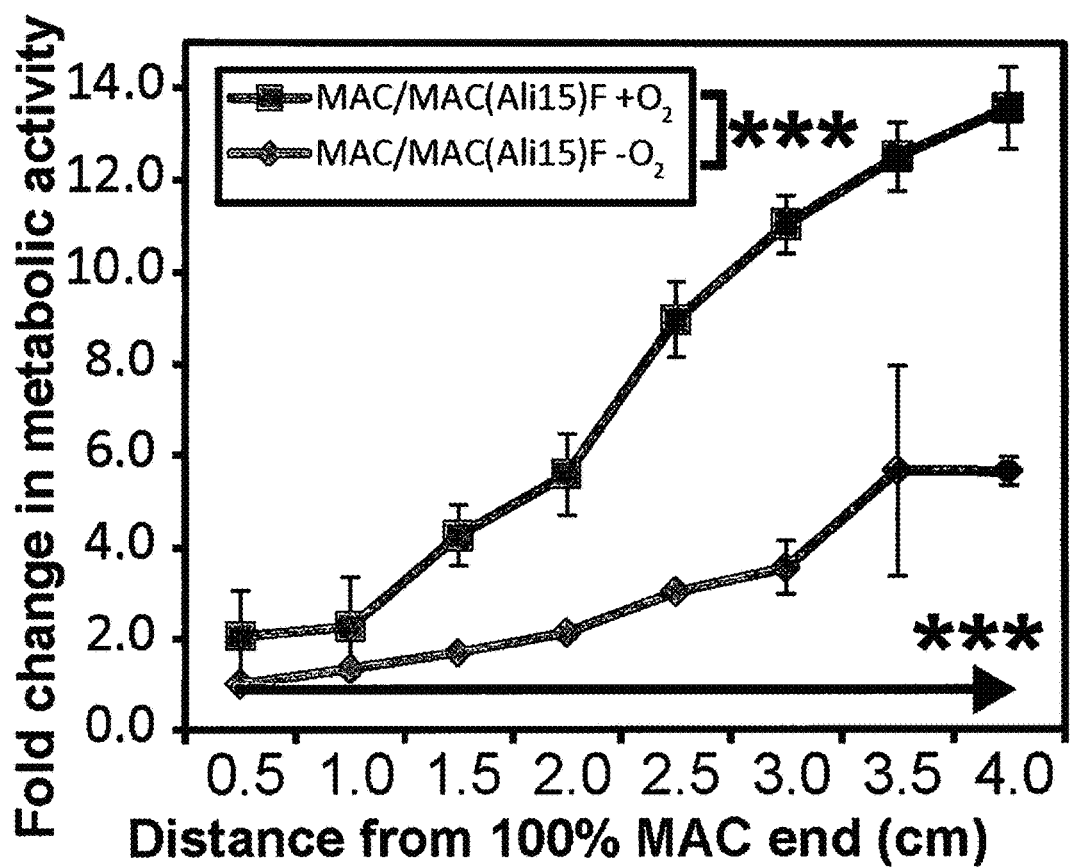
FIG. 17 provides a graph of one or more embodiments, MAC/MAC(Ali15)F, showing enhanced metabolism with more fluorine and supplemental oxygen. The results are reported as fold change compared with 100% MAC-$O_2$ regions. ***Significant difference by three-factor ANOVA (P<0.0001). All data n=3, means±SD.

Our work demonstrates that increasing the total number of conjugated fluorines enhances the total number of cells on MACF hydrogels (FIG. 14B), as well as the cellular metabolic activity (FIG. 14A and FIG. 15 to FIG. 16). Cell morphologies were more rounded than are typically seen on culture plates or stiffer hydrogels. However, active cellular responses were observed (FIG. 14) and they were independent of the stiffness of the underlying hydrogel. This suggests that local oxygenation overrides stiffness effects that have been reported previously on polymer substrates that do not enhance oxygen levels. Additionally, it is interesting that the enhanced metabolism and cellularity was independent of oxygen reloading during the culture period. These findings are fascinating, and we do not believe this result has been reported before with colloidal PFC systems. These results suggest to us that PFC modifications facilitate oxygen retrieval from the surrounding medium/air, making oxygen more available to cells. The metabolic responses on gradient surfaces of each MACF (FIG. 15 to FIG. 17) demonstrate that MACF-mediated oxygen levels are sensitive enough to change the cellular proliferation responses on a spatial scale of millimeters, if not less. This could be extremely valuable for modeling in vitro environments where oxygen gradients drive developmental and repair responses, such as vascularization and fracture healing. It is important to point out that cellular responses were enhanced with more fluorines per addition (FIG. 14 to FIG. 17), as well as better responses to MAC(Ar5)F vs. MAC(Ali5)F, however, these responses were not as different as were the $O_2$ uptake/release data for each material (FIG. 7 to FIG. 10). We believe this is due to the fact that the uptake and release experiments were performed in a closed system, whereas the cell experiments were carried out in an open system. At the outset the transport driving forces were greater in the uptake/release experiments, resulting in enhanced $O_2$ transport in groups with a more ideal PFC modification.

Our oxygen delivery approach using a biomaterial is unique compared with previous work and our system allows great flexibility. We believe that the application of our MACF system for deep wounds could support prolonged cell survival until host neovascularization is achieved. Our polymer MAC has been shown to exhibit 50% degradation after 28 days under physiological enzyme conditions, thus MACFs should provide days, if not weeks, of wound healing benefits. Since PFCs dissolve oxygen as well as other oxygenated species, like NO, $CO_2$ and CO, MACFs can be utilized to not only deliver oxygen but other beneficial gases, to scavenge waste gases or to reduce exposure to reactive oxygen species. Besides PFC emulsions, other works centered on oxygen delivery have studied biomaterials that facilitate oxygen generating reactions. Recent work has demonstrated that encapsulated calcium peroxide and perchlorocarbonates can create oxygen upon contact with an aqueous solution. However, the by-products produced are biologically unfavorable and are known to accumulate in tissues. In addition, peroxide decomposition is rapid and therefore can generate excessive amounts of oxygen as well as energy. As a result, concentrations of the oxygen generating reactants need to be carefully monitored to avoid harmful levels of oxidative stress. Lastly, in these oxygen generating systems the peroxide decomposition process also changes the local pH level, potentially creating a harmful environment if improperly buffered.

4. Conclusions

In this study we report the development of biocompatible, clinically relevant, highly tunable oxygen-rich biomaterials. This new class of fluorinated and biologically derived chitosan materials can be formed into injectable or moldable photocrosslinked hydrogels. Our approach deviates from existing methods (e.g., PFC suspensions or oxygen generators) as we can control the oxygen content inside the hydrogel by modifying the type of PFC substitution in the hydrogel network. This allows us to control both the capacity and rate of oxygen delivery, providing beneficial $PO_2$ levels for up to 5 days. Since these systems are capable of reloading oxygen more than once, they can be utilized for long periods of time (potentially weeks). We show that fibroblasts respond favorably to enhanced oxygen environments created by MACFs, even without supplemental oxygen, which should directly translate to accelerated wound healing in vivo.

What is claimed is:

1. A hydrogel comprising:
crosslinked polymers, the polymers having polysaccharide backbone chains, wherein the polysaccharide backbone chains have a pendant fluorine group attached thereto; and
wherein the polysaccharide backbone chains include one or more saccharide units that include an alkene group selected from the group consisting of:

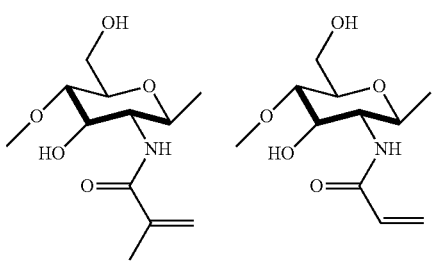

-continued

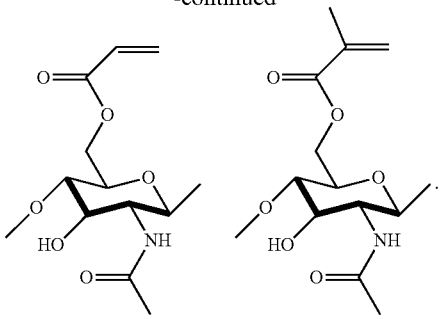

2. The hydrogel of claim 1, wherein the polysaccharide backbone chains have a pendant acetylamino group attached thereto.

3. The hydrogel of claim 1, wherein the polysaccharide backbone chains have a pendant amino group attached thereto.

4. The hydrogel of claim 1, wherein the polysaccharide backbone chains include one or more saccharide units selected from the group consisting of chitosan, dextran, hyaluronic acid, agarose, alginate, starch, cellulose, glycogen, carrageenans, galactomannans and combinations thereof.

5. The hydrogel of claim 1, wherein the pendant fluorine group is selected from the group consisting of:
   fluorocarbon groups;
   carbonyl groups defined by the formula:

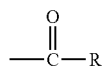

where R is a fluorocarbon group; and
carboxylate groups defined by the formula:

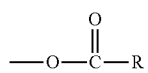

where R is a fluorocarbon group.

6. The hydrogel of claim 5, wherein the pendant fluorine group is a fluorocarbon group defined by the formula:

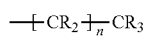

where each R is individually a hydrogen atom, or a fluorine atom.

7. The hydrogel of claim 5, wherein the pendant fluorine group is a fluorocarbon group defined by the formula:

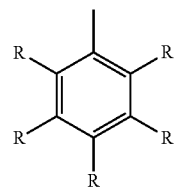

where each R is individually a hydrogen atom, a fluorine atom, a hydroxyl group, a hydrocarbon group, or a fluorocarbon group.

8. The hydrogel of claim 1, wherein the pendant fluorine group is an aromatic fluorocarbon group selected from the group consisting of:

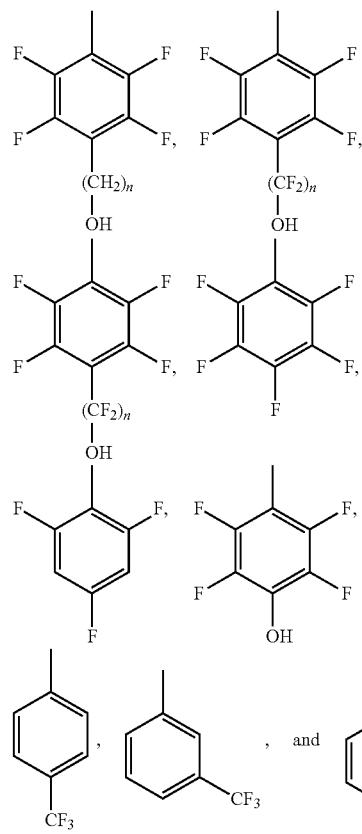

where n is 0 to 9.

9. The hydrogel of claim 1, where the crosslinked polymers are prepared by crosslinking a random copolymer of saccharide units defined by the formula:

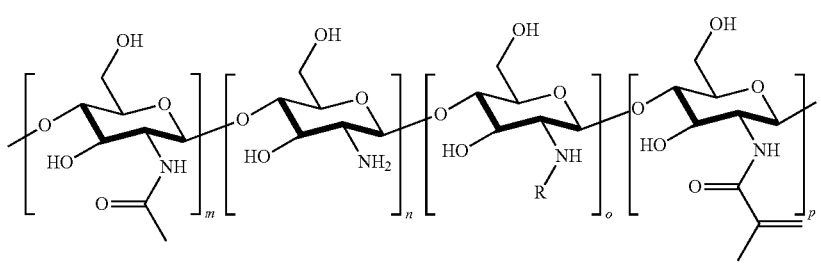

where R is a fluorine group, m is about 10% to about 20% of the total saccharide units, n is about 15% to about 70% of the total saccharide units, o is about 10% to about 40% of the total saccharide units, and p is about 10% to about 25% of the total saccharide units.

10. A hydrogel comprising:

a crosslinked polysaccharide, wherein the polysaccharide has a pendant fluorine group attached to a polysaccharide chain, wherein the pendant fluorine group is selected from the group consisting of:

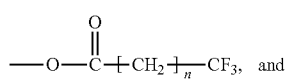

and

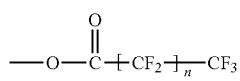

where n is 0 to 20.

11. The hydrogel of claim 10, wherein the pendant fluorine group is attached to the polysaccharide backbone chain via a polysaccharide unit defined by the formula:

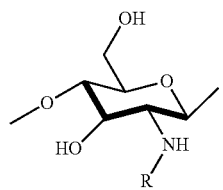

where R is said fluorine group.

12. A hydrogel comprising:

crosslinked polymers, the polymers having polysaccharide backbone chains, wherein the polysaccharide backbone chains have a pendant fluorine group attached thereto; and wherein the crosslinked polymer is selected from the group consisting of pentafluoropropionic anhydride modified methacrylamide chitosan, 2,3,4,5,6-pentafluorobenzaldehyde modified methacrylamide chitosan, and pentadecafluorooctanoyl chloride modified methacrylamide chitosan.

13. A hydrogel comprising:

crosslinked polymers, the polymers having polysaccharide backbone chains, wherein the polysaccharide backbone chains have a pendant fluorine group attached thereto; and wherein, prior to being crosslinked, the polysaccharide backbone chains include one or more saccharide units that include an alkene group selected from the group consisting of:

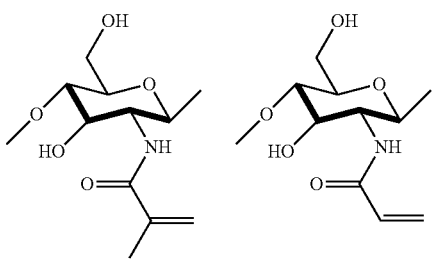

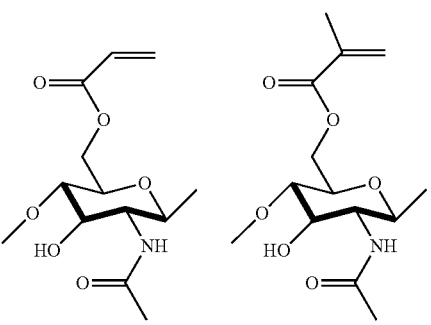

wherein, in the crosslinked polymers, said alkene group forms a covalent bond crosslink.

14. A method of preparing a hydrogel comprising: crosslinking a polymer, the polymer having polysaccharide backbone chains, wherein the polysaccharide backbone chains have a pendant fluorine group attached thereto; and wherein the polysaccharide backbone chains include one or more saccharide units that include an alkene group selected from the group consisting of:

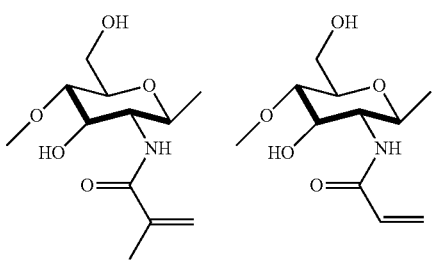

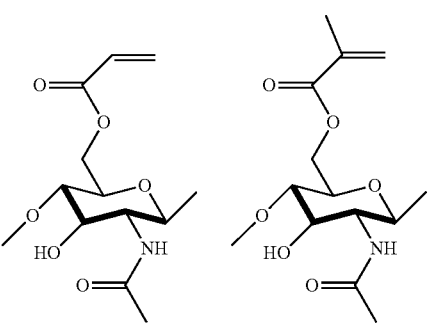

15. The method of claim 14, wherein the step of cross-linking the polymer is initiated by photoinitiation.

16. The method of claim 14, wherein the pendant fluorine group is selected from the group consisting of:
fluorocarbon groups;
carbonyl groups defined by the formula:

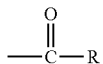

where R is a fluorocarbon group; and
carboxylate groups defined by the formula:

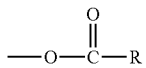

where R is a fluorocarbon group.

17. The method of claim 14, wherein the pendant fluorine group is a fluorocarbon group defined by the formula:

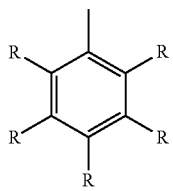

where each R is individually a hydrogen atom, a fluorine atom, a hydroxyl group, a hydrocarbon group, or a fluorocarbon group.

18. The method of claim 14, wherein the pendant fluorine group is aromatic fluorocarbon group selected from the group consisting of:

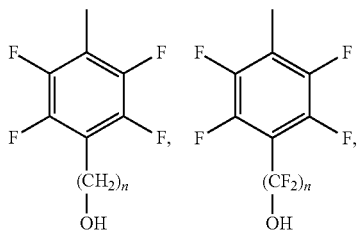

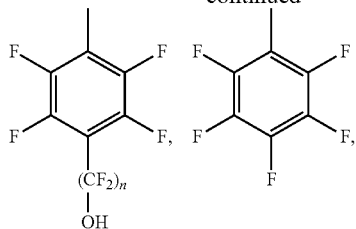

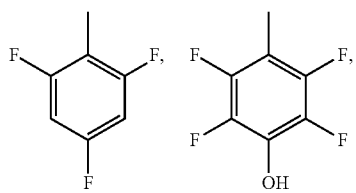

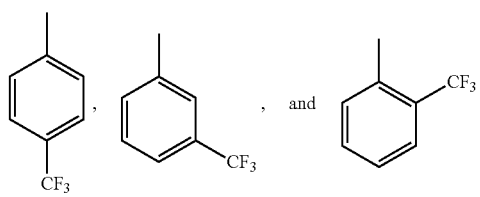

where n is 0 to 9.

19. The method of claim 14, wherein the pendant fluorine group is a carboxylate group selected from the group consisting of:

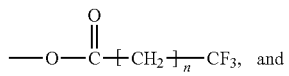

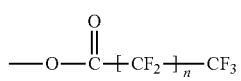

where n is 0 to 20.

20. The method of claim 14, wherein the polysaccharide backbone chains include a random copolymer of saccharide units defined by the formula:

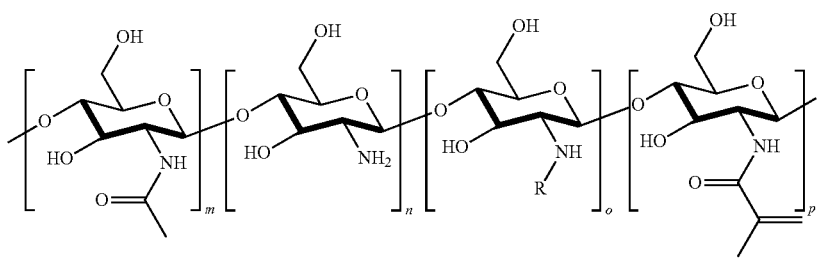

where R is a fluorine group, m is about 10% to about 20% of the total saccharide units, n is about 15% to about 70% of the total saccharide units, o is about 10% to about 40% of the total saccharide units, and p is about 10% to about 25% of the total saccharide units.

* * * * *